US012653426B2

(12) United States Patent
Desborough et al.

(10) Patent No.: US 12,653,426 B2
(45) Date of Patent: *Jun. 16, 2026

(54) MULTI-SCALE DISPLAY OF BLOOD GLUCOSE INFORMATION

(71) Applicant: Bigfoot Biomedical, Inc., Milpitas, CA (US)

(72) Inventors: Lane Desborough, Thousand Oaks, CA (US); Bryan Mazlish, Palo Alto, CA (US); Sabine Kabel-Eckes, Mountain View, CA (US); Jeff Boissier, San Jose, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 905 days.

This patent is subject to a terminal disclaimer.

(21) Appl. No.: 16/035,206

(22) Filed: Jul. 13, 2018

(65) Prior Publication Data

US 2019/0015024 A1 Jan. 17, 2019

Related U.S. Application Data

(60) Provisional application No. 62/532,167, filed on Jul. 13, 2017.

(51) Int. Cl.
*A61B 5/145* (2006.01)
*A61B 5/00* (2006.01)
(Continued)

(52) U.S. Cl.
CPC .......... *A61B 5/14532* (2013.01); *A61B 5/742* (2013.01); *A61M 5/003* (2013.01);
(Continued)

(58) Field of Classification Search
None
See application file for complete search history.

(56) References Cited

U.S. PATENT DOCUMENTS 303,013 A 8/1884 Horton
445,545 A 2/1891 Crane
(Continued)

FOREIGN PATENT DOCUMENTS

AU 2015200834 A1 3/2015
CA 2543545 A1 5/2005
(Continued)

OTHER PUBLICATIONS

US 5,954,699 A, 09/1999, Jost et al. (withdrawn)
(Continued)

*Primary Examiner* — Meredith Weare
(74) *Attorney, Agent, or Firm* — TraskBritt

(57) ABSTRACT

A system for displaying blood glucose information includes a blood glucose monitoring device configured to monitor blood glucose levels of a user, and a display. The system may also include one or more processors, and a non-transitory computer-readable medium containing instructions that, when executed by the one or more processors, cause the system to perform operations. The operations may include obtaining the blood glucose levels from the blood glucose monitoring device, where the blood glucose levels include at least a current blood glucose level and a historic blood glucose level. The operations may also include presenting the current blood glucose level at a first location on the display based on a first scale, and presenting the historic blood glucose level at a second location on the display based on a second scale different from the first scale.

17 Claims, 8 Drawing Sheets

(51) Int. Cl.

| | |
|---|---|
| *A61M 5/00* | (2006.01) |
| *A61M 5/142* | (2006.01) |
| *A61M 5/172* | (2006.01) |
| *G16H 20/17* | (2018.01) |
| *G16H 40/63* | (2018.01) |
| *G16H 50/30* | (2018.01) |

(52) U.S. Cl.
CPC ...... *A61M 5/14248* (2013.01); *A61M 5/1723* (2013.01); *G16H 20/17* (2018.01); *G16H 40/63* (2018.01); *G16H 50/30* (2018.01); *A61B 5/4836* (2013.01); *A61B 5/7275* (2013.01); *A61B 5/744* (2013.01); *A61M 2005/14272* (2013.01); *A61M 2005/14296* (2013.01); *A61M 2205/505* (2013.01); *A61M 2205/52* (2013.01); *A61M 2230/201* (2013.01)

(56) References Cited

U.S. PATENT DOCUMENTS

| | | | |
|---|---|---|---|
| 588,583 | A | 8/1897 | Lade |
| 1,441,508 | A | 1/1923 | Marius et al. |
| 2,283,925 | A | 5/1942 | Harvey |
| 2,605,765 | A | 8/1952 | Kollsman |
| 2,797,149 | A | 6/1957 | Skeggs |
| 2,886,529 | A | 5/1959 | Guillaud |
| 3,413,573 | A | 11/1968 | Nathanson et al. |
| 3,574,114 | A | 4/1971 | Monforte |
| 3,614,554 | A | 10/1971 | Shield et al. |
| 3,631,847 | A | 1/1972 | Hobbs |
| 3,634,039 | A | 1/1972 | Brondy |
| 3,812,843 | A | 5/1974 | Wootten et al. |
| 3,841,328 | A | 10/1974 | Jensen |
| 3,885,662 | A | 5/1975 | Schaefer |
| 3,886,938 | A | 6/1975 | Szabo et al. |
| 3,963,380 | A | 6/1976 | Thomas et al. |
| 3,983,077 | A | 9/1976 | Fuller et al. |
| 4,055,175 | A | 10/1977 | Clemens et al. |
| 4,077,405 | A | 3/1978 | Haerten et al. |
| 4,108,177 | A | 8/1978 | Pistor |
| 4,146,029 | A | 3/1979 | Ellinwood, Jr. |
| 4,151,845 | A | 5/1979 | Clemens |
| 4,231,368 | A | 11/1980 | Becker |
| 4,245,634 | A | 1/1981 | Albisser et al. |
| 4,265,241 | A | 5/1981 | Portner et al. |
| 4,268,150 | A | 5/1981 | Chen |
| 4,295,176 | A | 10/1981 | Wittwer |
| 4,300,554 | A | 11/1981 | Hessberg et al. |
| 4,313,439 | A | 2/1982 | Babb et al. |
| 4,368,980 | A | 1/1983 | Aldred et al. |
| 4,373,527 | A | 2/1983 | Fischell |
| 4,398,908 | A | 8/1983 | Siposs |
| 4,400,683 | A | 8/1983 | Eda et al. |
| 4,403,984 | A | 9/1983 | Ash et al. |
| 4,424,720 | A | 1/1984 | Bucchianeri |
| 4,435,173 | A | 3/1984 | Siposs et al. |
| 4,443,218 | A | 4/1984 | Decant et al. |
| 4,464,170 | A | 8/1984 | Clemens et al. |
| 4,469,481 | A | 9/1984 | Kobayashi |
| 4,475,901 | A | 10/1984 | Kraegen et al. |
| 4,493,704 | A | 1/1985 | Beard et al. |
| 4,498,843 | A | 2/1985 | Schneider et al. |
| 4,507,115 | A | 3/1985 | Kambara et al. |
| 4,523,170 | A | 6/1985 | Huth, III |
| 4,526,568 | A | 7/1985 | Clemens et al. |
| 4,526,569 | A | 7/1985 | Bernardi |
| 4,529,401 | A | 7/1985 | Leslie et al. |
| 4,551,134 | A | 11/1985 | Slavik et al. |
| 4,559,033 | A | 12/1985 | Stephen et al. |
| 4,559,037 | A | 12/1985 | Franetzki et al. |
| 4,562,751 | A | 1/1986 | Nason et al. |
| 4,573,968 | A | 3/1986 | Parker |
| 4,585,439 | A | 4/1986 | Michel |
| 4,601,707 | A | 7/1986 | Albisser et al. |
| 4,624,661 | A | 11/1986 | Arimond |
| 4,633,878 | A | 1/1987 | Bombardieri |
| 4,634,427 | A | 1/1987 | Hannula et al. |
| 4,646,038 | A | 2/1987 | Wanat |
| 4,657,529 | A | 4/1987 | Prince et al. |
| 4,678,408 | A | 7/1987 | Nason et al. |
| 4,681,569 | A | 7/1987 | Coble et al. |
| 4,684,368 | A | 8/1987 | Kenyon |
| 4,685,903 | A | 8/1987 | Cable et al. |
| 4,731,726 | A | 3/1988 | Allen, III |
| 4,743,243 | A | 5/1988 | Vaillancourt |
| 4,749,109 | A | 6/1988 | Kamen |
| 4,755,169 | A | 7/1988 | Sarnoff et al. |
| 4,755,173 | A | 7/1988 | Konopka et al. |
| 4,759,120 | A | 7/1988 | Bernstein |
| 4,781,688 | A | 11/1988 | Thoma et al. |
| 4,781,693 | A | 11/1988 | Martinez et al. |
| 4,808,161 | A | 2/1989 | Kamen |
| 4,838,857 | A | 6/1989 | Strowe et al. |
| 4,850,817 | A | 7/1989 | Nason et al. |
| 4,854,170 | A | 8/1989 | Brimhall et al. |
| 4,859,492 | A | 8/1989 | Rogers et al. |
| 4,880,770 | A | 11/1989 | Mir et al. |
| 4,886,499 | A | 12/1989 | Cirelli et al. |
| 4,898,578 | A | 2/1990 | Rubalcaba, Jr. |
| 4,898,579 | A | 2/1990 | Groshong et al. |
| 4,900,292 | A | 2/1990 | Berry et al. |
| 4,919,596 | A | 4/1990 | Slate et al. |
| 4,925,444 | A | 5/1990 | Orkin et al. |
| 4,940,527 | A | 7/1990 | Kazlauskas et al. |
| 4,944,659 | A | 7/1990 | Labbe et al. |
| 4,967,201 | A | 10/1990 | Rich, III |
| 4,969,874 | A | 11/1990 | Michel et al. |
| 4,975,581 | A | 12/1990 | Robinson et al. |
| 4,976,720 | A | 12/1990 | Machold et al. |
| 4,981,140 | A | 1/1991 | Wyatt |
| 4,994,047 | A | 2/1991 | Walker et al. |
| 5,007,286 | A | 4/1991 | Malcolm et al. |
| 5,007,458 | A | 4/1991 | Marcus et al. |
| 5,045,064 | A | 9/1991 | Idriss |
| 5,061,424 | A | 10/1991 | Karimi et al. |
| 5,062,841 | A | 11/1991 | Siegel |
| 5,084,749 | A | 1/1992 | Losee et al. |
| 5,088,981 | A | 2/1992 | Howson et al. |
| 5,088,990 | A | 2/1992 | Hivale et al. |
| 5,097,834 | A | 3/1992 | Skrabal |
| D325,781 | S | 4/1992 | Moller-Jensen |
| 5,102,406 | A | 4/1992 | Arnold |
| 5,109,850 | A | 5/1992 | Blanco et al. |
| 5,125,415 | A | 6/1992 | Bell |
| 5,130,675 | A | 7/1992 | Sugawara |
| 5,134,079 | A | 7/1992 | Cusack et al. |
| 5,139,999 | A | 8/1992 | Gordon et al. |
| 5,153,827 | A | 10/1992 | Coutre et al. |
| 5,154,973 | A | 10/1992 | Imagawa et al. |
| 5,165,406 | A | 11/1992 | Wong |
| 5,176,662 | A | 1/1993 | Bartholomew et al. |
| 5,178,609 | A | 1/1993 | Ishikawa |
| 5,189,609 | A | 2/1993 | Tivig et al. |
| 5,190,522 | A | 3/1993 | Wojcicki et al. |
| 5,198,824 | A | 3/1993 | Poradish |
| 5,205,819 | A | 4/1993 | Ross et al. |
| 5,207,642 | A | 5/1993 | Orkin et al. |
| 5,213,483 | A | 5/1993 | Flaherty et al. |
| 5,217,754 | A | 6/1993 | Santiago-Aviles et al. |
| 5,219,377 | A | 6/1993 | Poradish |
| 5,225,763 | A | 7/1993 | Krohn et al. |
| 5,232,439 | A | 8/1993 | Campbell et al. |
| 5,237,993 | A | 8/1993 | Skrabal |
| 5,244,463 | A | 9/1993 | Cordner et al. |
| 5,250,027 | A | 10/1993 | Lewis et al. |
| 5,254,096 | A | 10/1993 | Rondelet et al. |
| 5,257,980 | A | 11/1993 | Van et al. |
| 5,261,882 | A | 11/1993 | Sealfon |
| 5,263,198 | A | 11/1993 | Geddes et al. |
| 5,272,485 | A | 12/1993 | Mason et al. |
| 5,273,517 | A | 12/1993 | Barone et al. |
| 5,281,202 | A | 1/1994 | Weber et al. |
| 5,281,808 | A | 1/1994 | Kunkel |

US 12,653,426 B2

Page 3

(56)                    References Cited

U.S. PATENT DOCUMENTS 5,299,571  A     4/1994   Mastrototaro
5,308,982  A     5/1994   Ivaldi et al.
5,314,412  A     5/1994   Rex
5,335,994  A     8/1994   Weynant nee Girones
5,338,157  A     8/1994   Blomquist
5,342,180  A     8/1994   Daoud
5,342,298  A     8/1994   Michaels et al.
5,346,476  A     9/1994   Elson
D351,469   S    10/1994   Okamoto
5,364,342  A    11/1994   Beuchat et al.
5,377,674  A     1/1995   Kuestner
5,380,665  A     1/1995   Cusack et al.
5,385,539  A     1/1995   Maynard
5,389,078  A     2/1995   Zalesky et al.
5,395,340  A     3/1995   Lee
5,403,797  A     4/1995   Ohtani et al.
5,411,487  A     5/1995   Castagna
5,411,889  A     5/1995   Hoots et al.
5,421,812  A     6/1995   Langley et al.
5,427,988  A     6/1995   Sengupta et al.
5,433,710  A     7/1995   Vanantwerp et al.
5,456,945  A    10/1995   Mcmillan et al.
5,468,727  A    11/1995   Phillips et al.
5,478,610  A    12/1995   Desu et al.
5,505,709  A     4/1996   Funderburk et al.
5,505,828  A     4/1996   Wong et al.
5,507,288  A     4/1996   Boecker et al.
5,513,382  A     4/1996   Agahi-Kesheh et al.
5,533,389  A     7/1996   Kamen et al.
5,535,445  A     7/1996   Gunton
5,540,772  A     7/1996   Mcmillan et al.
5,543,773  A     8/1996   Evans et al.
5,545,143  A     8/1996   Fischell et al.
5,551,850  A     9/1996   Williamson et al.
5,554,123  A     9/1996   Herskowitz
5,558,640  A     9/1996   Pfeiler et al.
5,569,186  A    10/1996   Lord et al.
5,582,593  A    12/1996   Hultman
5,584,053  A    12/1996   Kommrusch et al.
5,584,813  A    12/1996   Livingston et al.
5,590,387  A    12/1996   Schmidt et al.
5,609,572  A     3/1997   Lang
5,614,252  A     3/1997   Mcmillan et al.
5,625,365  A     4/1997   Tom et al.
5,626,566  A     5/1997   Petersen et al.
5,635,433  A     6/1997   Sengupta
5,637,095  A     6/1997   Nason et al.
5,640,954  A     6/1997   Pfeiffer et al.
5,665,065  A     9/1997   Colman et al.
5,665,070  A     9/1997   Mcphee
5,678,539  A    10/1997   Schubert et al.
5,678,571  A    10/1997   Brown
5,685,844  A    11/1997   Marttila
5,685,859  A    11/1997   Kornerup
5,693,018  A    12/1997   Kriesel et al.
5,697,899  A    12/1997   Hillman et al.
5,700,695  A    12/1997   Yassinzadeh et al.
5,703,364  A    12/1997   Rosenthal
5,707,459  A     1/1998   Itoyama et al.
5,707,715  A     1/1998   Derochemont et al.
5,713,875  A     2/1998   Tanner, II
5,714,123  A     2/1998   Sohrab
5,716,343  A     2/1998   Kriesel et al.
5,718,562  A     2/1998   Lawless et al.
5,722,397  A     3/1998   Eppstein
D393,264   S     4/1998   Leung
5,741,216  A     4/1998   Hemmingsen et al.
5,741,228  A     4/1998   Lambrecht et al.
5,746,217  A     5/1998   Erickson et al.
5,747,350  A     5/1998   Sattler
5,747,870  A     5/1998   Pedder
5,748,827  A     5/1998   Holl et al.
5,755,682  A     5/1998   Knudson et al.
5,758,643  A     6/1998   Wong et al.
5,759,923  A     6/1998   Mcmillan et al.

5,764,189  A     6/1998   Lohninger
5,766,155  A     6/1998   Hyman et al.
5,771,567  A     6/1998   Pierce et al.
5,772,635  A     6/1998   Dastur et al.
5,776,103  A     7/1998   Kriesel et al.
5,779,676  A     7/1998   Kriesel et al.
5,785,688  A     7/1998   Joshi et al.
5,797,881  A     8/1998   Gadot
5,800,397  A     9/1998   Wilson et al.
5,800,405  A     9/1998   Mcphee
5,800,420  A     9/1998   Gross et al.
5,801,057  A     9/1998   Smart et al.
5,804,048  A     9/1998   Wong et al.
5,807,075  A     9/1998   Jacobsen et al.
5,816,306  A    10/1998   Giacomel
5,817,007  A    10/1998   Fodgaard et al.
5,820,622  A    10/1998   Gross et al.
5,822,715  A    10/1998   Worthington et al.
5,823,951  A    10/1998   Messerschmidt
5,839,467  A    11/1998   Saaski et al.
5,840,020  A    11/1998   Heinonen et al.
D403,313   S    12/1998   Peppel
5,848,991  A    12/1998   Gross et al.
5,851,197  A    12/1998   Marano et al.
5,852,803  A    12/1998   Ashby et al.
5,854,608  A    12/1998   Leisten
5,858,001  A     1/1999   Tsals et al.
5,858,005  A     1/1999   Kriesel
5,858,239  A     1/1999   Kenley et al.
5,859,621  A     1/1999   Leisten
5,865,806  A     2/1999   Howell
5,871,470  A     2/1999   Mcwha
5,879,310  A     3/1999   Sopp et al.
5,889,459  A     3/1999   Hattori et al.
5,891,097  A     4/1999   Saito et al.
5,892,489  A     4/1999   Kanba et al.
5,897,530  A     4/1999   Jackson
5,902,253  A     5/1999   Pfeiffer et al.
5,903,421  A     5/1999   Furutani et al.
5,906,597  A     5/1999   Mcphee
5,911,716  A     6/1999   Rake et al.
5,918,603  A     7/1999   Brown
5,919,167  A     7/1999   Mulhauser et al.
5,925,018  A     7/1999   Ungerstedt
5,928,201  A     7/1999   Poulsen et al.
5,931,814  A     8/1999   Alex et al.
5,932,175  A     8/1999   Knute et al.
5,933,121  A     8/1999   Rainhart et al.
5,935,099  A     8/1999   Peterson et al.
5,945,963  A     8/1999   Leisten
5,947,911  A     9/1999   Wong et al.
5,947,934  A     9/1999   Hansen et al.
5,951,530  A     9/1999   Steengaard et al.
5,957,889  A     9/1999   Poulsen et al.
5,957,890  A     9/1999   Mann et al.
5,961,492  A    10/1999   Kriesel et al.
5,965,848  A    10/1999   Altschul et al.
5,971,941  A    10/1999   Simons et al.
5,984,894  A    11/1999   Poulsen et al.
5,984,897  A    11/1999   Petersen et al.
5,993,423  A    11/1999   Choi
5,997,475  A    12/1999   Bortz
5,997,501  A    12/1999   Gross et al.
6,003,736  A    12/1999   Ljunggren
6,005,151  A    12/1999   Herrmann et al.
6,010,485  A     1/2000   Buch-Rasmussen et al.
6,017,318  A     1/2000   Gauthier et al.
6,019,747  A     2/2000   Mcphee
6,023,251  A     2/2000   Koo et al.
6,024,539  A     2/2000   Blomquist
6,027,826  A     2/2000   Derochemont et al.
6,028,568  A     2/2000   Asakura et al.
6,031,445  A     2/2000   Marty et al.
6,032,059  A     2/2000   Henning et al.
6,032,119  A     2/2000   Brown et al.
6,033,377  A     3/2000   Rasmussen et al.
6,036,924  A     3/2000   Simons et al.
6,040,578  A     3/2000   Malin et al.
6,040,805  A     3/2000   Huynh et al.

(56) References Cited

U.S. PATENT DOCUMENTS

| | | | |
|---|---|---|---|
| 6,045,537 A | 4/2000 | Klitmose |
| 6,046,707 A | 4/2000 | Gaughan et al. |
| 6,049,727 A | 4/2000 | Crothall |
| 6,050,978 A | 4/2000 | Orr et al. |
| 6,052,040 A | 4/2000 | Hino |
| D424,036 S | 5/2000 | Arora et al. |
| 6,056,728 A | 5/2000 | von Schuckmann |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,074,372 A | 6/2000 | Hansen |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,110,149 A | 8/2000 | Klitgaard et al. |
| 6,111,544 A | 8/2000 | Dakeya et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,143,432 A | 11/2000 | De et al. |
| 6,154,176 A | 11/2000 | Fathy et al. |
| 6,156,014 A | 12/2000 | Petersen et al. |
| 6,157,041 A | 12/2000 | Thomas et al. |
| 6,161,028 A | 12/2000 | Braig et al. |
| 6,162,639 A | 12/2000 | Douglas |
| 6,171,276 B1 | 1/2001 | Lippe et al. |
| 6,174,300 B1 | 1/2001 | Kriesel et al. |
| 6,176,004 B1 | 1/2001 | Rainhart et al. |
| 6,181,297 B1 | 1/2001 | Leisten |
| 6,188,368 B1 | 2/2001 | Koriyama et al. |
| 6,190,359 B1 | 2/2001 | Heruth |
| 6,195,049 B1 | 2/2001 | Kim et al. |
| 6,196,046 B1 | 3/2001 | Braig et al. |
| 6,200,287 B1 | 3/2001 | Keller et al. |
| 6,200,293 B1 | 3/2001 | Kriesel et al. |
| 6,200,338 B1 | 3/2001 | Solomon et al. |
| 6,204,203 B1 | 3/2001 | Narwankar et al. |
| 6,208,843 B1 | 3/2001 | Huang et al. |
| 6,214,629 B1 | 4/2001 | Freitag et al. |
| 6,222,489 B1 | 4/2001 | Tsuru et al. |
| 6,226,082 B1 | 5/2001 | Roe |
| 6,231,540 B1 | 5/2001 | Smedegaard |
| 6,244,776 B1 | 6/2001 | Wiley |
| 6,248,067 B1 | 6/2001 | Causey et al. |
| 6,248,090 B1 | 6/2001 | Jensen et al. |
| 6,248,093 B1 | 6/2001 | Moberg |
| 6,261,065 B1 | 7/2001 | Nayak et al. |
| 6,262,798 B1 | 7/2001 | Shepherd et al. |
| 6,266,020 B1 | 7/2001 | Chang |
| 6,270,455 B1 | 8/2001 | Brown |
| 6,271,045 B1 | 8/2001 | Douglas et al. |
| 6,277,098 B1 | 8/2001 | Klitmose et al. |
| 6,280,381 B1 | 8/2001 | Malin et al. |
| 6,285,448 B1 | 9/2001 | Kuenstner |
| 6,300,894 B1 | 10/2001 | Lynch et al. |
| 6,302,855 B1 | 10/2001 | Lav et al. |
| 6,302,869 B1 | 10/2001 | Klitgaard |
| 6,309,370 B1 | 10/2001 | Haim et al. |
| 6,312,888 B1 | 11/2001 | Wong et al. |
| 6,320,547 B1 | 11/2001 | Fathy et al. |
| 6,323,549 B1 | 11/2001 | Derochemont et al. |
| 6,334,851 B1 | 1/2002 | Hayes et al. |
| 6,354,996 B1 | 3/2002 | Drinan et al. |
| 6,363,609 B1 | 4/2002 | Pickren |
| 6,368,314 B1 | 4/2002 | Kipfer et al. |
| 6,375,627 B1 | 4/2002 | Mauze et al. |
| 6,375,638 B2 | 4/2002 | Nason et al. |
| 6,379,301 B1 | 4/2002 | Worthington et al. |
| 6,379,339 B1 | 4/2002 | Klitgaard et al. |
| 6,381,496 B1 | 4/2002 | Meadows et al. |
| 6,402,689 B1 | 6/2002 | Scarantino et al. |
| 6,404,098 B1 | 6/2002 | Kayama et al. |
| D460,053 S | 7/2002 | Choi |
| 6,413,244 B1 | 7/2002 | Bestetti et al. |
| 6,427,088 B1 | 7/2002 | Bowman et al. |
| D461,241 S | 8/2002 | Moberg et al. |
| D461,891 S | 8/2002 | Moberg |
| 6,436,072 B1 | 8/2002 | Kullas et al. |
| 6,461,331 B1 | 10/2002 | Van Antwerp |
| 6,470,279 B1 | 10/2002 | Samsoondar |
| 6,474,219 B2 | 11/2002 | Klitmose et al. |
| 6,475,196 B1 | 11/2002 | Vachon |
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,492,949 B1 | 12/2002 | Breglia et al. |
| 6,496,149 B1 | 12/2002 | Birnbaum et al. |
| 6,501,415 B1 | 12/2002 | Viana et al. |
| 6,508,788 B2 | 1/2003 | Preuthun |
| 6,512,937 B2 | 1/2003 | Blank et al. |
| 6,520,936 B1 | 2/2003 | Mann |
| 6,524,280 B2 | 2/2003 | Hansen et al. |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,533,183 B2 | 3/2003 | Aasmul et al. |
| 6,537,249 B2 | 3/2003 | Kriesell et al. |
| 6,537,251 B2 | 3/2003 | Klitmose |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |
| 6,544,229 B1 | 4/2003 | Danby et al. |
| 6,546,268 B1 | 4/2003 | Ishikawa et al. |
| 6,546,269 B1 | 4/2003 | Kurnik |
| 6,547,764 B2 | 4/2003 | Larsen et al. |
| 6,551,276 B1 | 4/2003 | Mann et al. |
| 6,552,693 B1 | 4/2003 | Leisten |
| 6,553,841 B1 | 4/2003 | Blouch |
| 6,554,798 B1 | 4/2003 | Mann et al. |
| 6,554,800 B1 | 4/2003 | Nezhadian et al. |
| 6,556,850 B1 | 4/2003 | Braig et al. |
| D474,778 S | 5/2003 | Barnes |
| 6,558,320 B1 | 5/2003 | Causey et al. |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,011 B1 | 5/2003 | Buch-Rasmussen et al. |
| 6,562,014 B2 | 5/2003 | Lin et al. |
| 6,564,105 B2 | 5/2003 | Starkweather et al. |
| 6,569,115 B1 | 5/2003 | Barker et al. |
| 6,569,125 B2 | 5/2003 | Jepson et al. |
| 6,569,126 B1 | 5/2003 | Poulsen et al. |
| 6,571,128 B2 | 5/2003 | Lebel et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,577,899 B2 | 6/2003 | Lebel et al. |
| 6,580,934 B1 | 6/2003 | Braig et al. |
| 6,582,404 B1 | 6/2003 | Klitgaard et al. |
| 6,583,699 B2 | 6/2003 | Yokoyama |
| 6,585,644 B2 | 7/2003 | Lebel et al. |
| 6,585,699 B2 | 7/2003 | Ljunggreen et al. |
| 6,589,229 B1 | 7/2003 | Connelly et al. |
| 6,595,956 B1 | 7/2003 | Gross et al. |
| 6,605,067 B1 | 8/2003 | Larsen |
| 6,611,419 B1 | 8/2003 | Chakravorty |
| 6,613,019 B2 | 9/2003 | Munk |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |

(56) References Cited

U.S. PATENT DOCUMENTS

| | | | |
|---|---|---|---|
| 6,639,556 B2 | 10/2003 | Baba |
| 6,641,533 B2 | 11/2003 | Causey et al. |
| 6,642,908 B2 | 11/2003 | Pleva et al. |
| 6,645,142 B2 | 11/2003 | Braig et al. |
| 6,648,821 B2 | 11/2003 | Lebel et al. |
| 6,650,303 B2 | 11/2003 | Kim et al. |
| 6,650,951 B1 | 11/2003 | Jones et al. |
| 6,653,091 B1 | 11/2003 | Dunn et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,662,030 B2 | 12/2003 | Khalil et al. |
| 6,663,602 B2 | 12/2003 | Moeller |
| 6,668,196 B1 | 12/2003 | Villegas et al. |
| 6,669,663 B1 | 12/2003 | Thompson |
| 6,669,669 B2 | 12/2003 | Flaherty et al. |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,686,406 B2 | 2/2004 | Tomomatsu et al. |
| 6,687,546 B2 | 2/2004 | Lebel et al. |
| 6,690,192 B1 | 2/2004 | Wing |
| 6,690,336 B1 | 2/2004 | Leisten et al. |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,702,779 B2 | 3/2004 | Connelly et al. |
| 6,715,516 B2 | 4/2004 | Ohms et al. |
| 6,716,198 B2 | 4/2004 | Larsen |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,446 B2 | 5/2004 | Lebel et al. |
| 6,733,890 B2 | 5/2004 | Imanaka et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,741,148 B2 | 5/2004 | Killen et al. |
| 6,742,249 B2 | 6/2004 | Derochemont et al. |
| 6,743,744 B1 | 6/2004 | Kim et al. |
| 6,744,350 B2 | 6/2004 | Blomquist |
| 6,749,587 B2 | 6/2004 | Flaherty |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,752,787 B1 | 6/2004 | Causey et al. |
| 6,753,745 B2 | 6/2004 | Killen et al. |
| 6,753,814 B2 | 6/2004 | Killen et al. |
| 6,758,810 B2 | 7/2004 | Lebel et al. |
| 6,758,835 B2 | 7/2004 | Close et al. |
| 6,762,237 B2 | 7/2004 | Glatkowski et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,787,181 B2 | 9/2004 | Uchiyama et al. |
| 6,791,496 B1 | 9/2004 | Killen et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman et al. |
| 6,813,519 B2 | 11/2004 | Lebel et al. |
| 6,826,031 B2 | 11/2004 | Nagai et al. |
| 6,827,702 B2 | 12/2004 | Lebel et al. |
| 6,830,558 B2 | 12/2004 | Flaherty et al. |
| 6,830,623 B2 | 12/2004 | Hayashi et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,852,104 B2 | 2/2005 | Blomquist |
| 6,853,288 B2 | 2/2005 | Ahn et al. |
| 6,854,620 B2 | 2/2005 | Ramey |
| 6,854,653 B2 | 2/2005 | Eilersen |
| 6,855,129 B2 | 2/2005 | Jensen et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,878,871 B2 | 4/2005 | Scher et al. |
| 6,883,778 B1 | 4/2005 | Newton et al. |
| 6,890,291 B2 | 5/2005 | Robinson et al. |
| 6,893,415 B2 | 5/2005 | Madsen et al. |
| 6,899,695 B2 | 5/2005 | Herrera |
| 6,899,699 B2 | 5/2005 | Enggaard |
| 6,905,989 B2 | 6/2005 | Ellis et al. |
| 6,906,674 B2 | 6/2005 | Mckinzie et al. |
| 6,914,566 B2 | 7/2005 | Beard |
| 6,919,119 B2 | 7/2005 | Kalkan et al. |
| 6,922,590 B1 | 7/2005 | Whitehurst |
| 6,928,298 B2 | 8/2005 | Furutani et al. |
| 6,936,006 B2 | 8/2005 | Sabra |
| 6,936,029 B2 | 8/2005 | Mann et al. |
| 6,943,430 B2 | 9/2005 | Kwon |
| 6,943,731 B2 | 9/2005 | Killen et al. |
| 6,945,961 B2 | 9/2005 | Miller et al. |
| 6,948,918 B2 | 9/2005 | Hansen |
| 6,949,081 B1 | 9/2005 | Chance |
| 6,950,708 B2 | 9/2005 | Bowman et al. |
| 6,956,572 B2 | 10/2005 | Zaleski |
| 6,958,809 B2 | 10/2005 | Sterling et al. |
| 6,960,192 B1 | 11/2005 | Flaherty et al. |
| 6,963,259 B2 | 11/2005 | Killen et al. |
| 6,979,326 B2 | 12/2005 | Mann et al. |
| 6,989,891 B2 | 1/2006 | Braig et al. |
| 6,990,366 B2 | 1/2006 | Say et al. |
| 6,997,911 B2 | 2/2006 | Klitmose |
| 6,997,920 B2 | 2/2006 | Mann et al. |
| 7,002,436 B2 | 2/2006 | Ma et al. |
| 7,005,078 B2 | 2/2006 | Van et al. |
| 7,008,399 B2 | 3/2006 | Larsen et al. |
| 7,008,404 B2 | 3/2006 | Nakajima |
| 7,009,180 B2 | 3/2006 | Sterling et al. |
| 7,014,625 B2 | 3/2006 | Bengtsson |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,029,455 B2 | 4/2006 | Flaherty |
| 7,043,288 B2 | 5/2006 | Davis et al. |
| 7,047,637 B2 | 5/2006 | Derochemont et al. |
| 7,054,836 B2 | 5/2006 | Christensen et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,096,124 B2 | 8/2006 | Sterling et al. |
| 7,096,431 B2 | 8/2006 | Tambata et al. |
| 7,104,972 B2 | 9/2006 | Moller et al. |
| 7,109,878 B2 | 9/2006 | Mann et al. |
| 7,115,205 B2 | 10/2006 | Robinson et al. |
| 7,116,949 B2 | 10/2006 | Irie et al. |
| 7,128,727 B2 | 10/2006 | Flaherty et al. |
| 7,133,329 B2 | 11/2006 | Skyggebjerg et al. |
| 7,137,694 B2 | 11/2006 | Ferran et al. |
| 7,139,593 B2 | 11/2006 | Kavak et al. |

(56)                    References Cited

U.S. PATENT DOCUMENTS

| | | | |
|---|---|---|---|
| 7,139,598 B2 | 11/2006 | Hull et al. | |
| 7,160,272 B1 | 1/2007 | Eyal et al. | |
| 7,171,252 B1 | 1/2007 | Scarantino et al. | |
| 7,190,988 B2 | 3/2007 | Say et al. | |
| 7,204,823 B2 | 4/2007 | Estes et al. | |
| 7,230,316 B2 | 6/2007 | Yamazaki et al. | |
| 7,232,423 B2 | 6/2007 | Morten | |
| D545,837 S | 7/2007 | Haldimann et al. | |
| 7,241,265 B2 | 7/2007 | Cummings et al. | |
| 7,248,912 B2 | 7/2007 | Gough et al. | |
| D550,227 S | 9/2007 | Sato et al. | |
| 7,267,665 B2 | 9/2007 | Steil et al. | |
| 7,271,912 B2 | 9/2007 | Sterling et al. | |
| D554,140 S | 10/2007 | Armendariz | |
| 7,278,983 B2 | 10/2007 | Ireland et al. | |
| 7,291,107 B2 | 11/2007 | Hellwig et al. | |
| 7,291,497 B2 | 11/2007 | Holmes et al. | |
| 7,291,782 B2 | 11/2007 | Sager et al. | |
| 7,303,622 B2 | 12/2007 | Loch et al. | |
| 7,303,922 B2 | 12/2007 | Jeng et al. | |
| 7,343,197 B2 | 3/2008 | Shusterman | |
| 7,354,420 B2 | 4/2008 | Steil et al. | |
| 7,388,202 B2 | 6/2008 | Sterling et al. | |
| 7,402,153 B2 | 7/2008 | Steil et al. | |
| 7,405,698 B2 | 7/2008 | de Rochemont | |
| 7,429,255 B2 | 9/2008 | Thompson | |
| 7,440,786 B2 | 10/2008 | Hockersmith et al. | |
| 7,454,359 B2 | 11/2008 | Rosenfeld et al. | |
| 7,460,130 B2 | 12/2008 | Salganicoff | |
| 7,481,787 B2 | 1/2009 | Gable et al. | |
| 7,491,187 B2 | 2/2009 | Van et al. | |
| 7,500,949 B2 | 3/2009 | Gottlieb et al. | |
| 7,509,156 B2 | 3/2009 | Flanders | |
| D590,415 S | 4/2009 | Ball et al. | |
| 7,522,124 B2 | 4/2009 | Smith et al. | |
| D592,223 S | 5/2009 | Neuhaus | |
| 7,534,226 B2 | 5/2009 | Mernoe et al. | |
| 7,547,281 B2 | 6/2009 | Hayes et al. | |
| 7,553,281 B2 | 6/2009 | Hellwig et al. | |
| 7,553,512 B2 | 6/2009 | Kodas et al. | |
| 7,564,887 B2 | 7/2009 | Wang et al. | |
| 7,569,030 B2 | 8/2009 | Lebel et al. | |
| 7,570,980 B2 | 8/2009 | Ginsberg | |
| D600,341 S | 9/2009 | Loerwald | |
| 7,595,623 B2 | 9/2009 | Bennett | |
| 7,608,042 B2 | 10/2009 | Goldberger et al. | |
| D603,421 S | 11/2009 | Ebeling et al. | |
| D607,099 S | 12/2009 | Loerwald | |
| 7,647,237 B2 | 1/2010 | Malave et al. | |
| 7,651,845 B2 | 1/2010 | Doyle et al. | |
| 7,652,901 B2 | 1/2010 | Kirchmeier et al. | |
| 7,680,529 B2 | 3/2010 | Kroll | |
| D614,587 S | 4/2010 | Yodfat et al. | |
| D614,634 S | 4/2010 | Nilsen | |
| 7,695,434 B2 | 4/2010 | Malecha | |
| 7,708,717 B2 | 5/2010 | Estes et al. | |
| 7,714,794 B2 | 5/2010 | Tavassoli Hozouri | |
| 7,717,903 B2 | 5/2010 | Estes et al. | |
| 7,734,323 B2 | 6/2010 | Blomquist et al. | |
| 7,751,907 B2 | 7/2010 | Blomquist | |
| 7,763,917 B2 | 7/2010 | de Rochemont | |
| 7,766,829 B2 | 8/2010 | Sloan et al. | |
| 7,771,391 B2 | 8/2010 | Carter | |
| 7,785,258 B2 | 8/2010 | Braig et al. | |
| D623,753 S | 9/2010 | Saffer et al. | |
| 7,789,859 B2 | 9/2010 | Estes et al. | |
| 7,806,854 B2 | 10/2010 | Damiano et al. | |
| 7,806,886 B2 | 10/2010 | Kanderian et al. | |
| 7,812,774 B2 | 10/2010 | Friman et al. | |
| 7,828,528 B2 | 11/2010 | Estes et al. | |
| 7,837,647 B2 | 11/2010 | Estes et al. | |
| 7,850,641 B2 | 12/2010 | Lebel et al. | |
| 7,871,376 B2 | 1/2011 | Brown | |
| 7,878,975 B2 | 2/2011 | Liljeryd et al. | |
| 7,887,512 B2 | 2/2011 | Estes et al. | |
| 7,918,825 B2 | 4/2011 | O'Connor et al. | |
| 7,931,613 B2 | 4/2011 | Haueter et al. | |
| 7,938,797 B2 | 5/2011 | Estes | |
| 7,946,985 B2 | 5/2011 | Mastrototaro et al. | |
| D640,269 S | 6/2011 | Chen | |
| D642,191 S | 7/2011 | Barnett et al. | |
| 7,972,296 B2 | 7/2011 | Braig et al. | |
| 8,012,119 B2 | 9/2011 | Estes et al. | |
| 8,066,805 B2 | 11/2011 | Zuercher et al. | |
| 8,069,690 B2 | 12/2011 | Desantolo et al. | |
| D652,426 S | 1/2012 | Anzures | |
| 8,114,489 B2 | 2/2012 | Nemat-Nasser et al. | |
| 8,132,101 B2 | 3/2012 | Buck et al. | |
| RE43,316 E | 4/2012 | Brown et al. | |
| D656,950 S | 4/2012 | Shallcross et al. | |
| 8,156,070 B2 | 4/2012 | Buck et al. | |
| D660,315 S | 5/2012 | Anzures | |
| 8,178,457 B2 | 5/2012 | De Rochemont | |
| D661,701 S | 6/2012 | Brown et al. | |
| 8,193,873 B2 | 6/2012 | Kato et al. | |
| 8,202,249 B2 | 6/2012 | Iio et al. | |
| 8,217,946 B2 | 7/2012 | Halpern et al. | |
| 8,219,222 B2 | 7/2012 | Blomquist | |
| 8,221,345 B2 | 7/2012 | Blomquist | |
| 8,231,562 B2 | 7/2012 | Buck et al. | |
| D665,409 S | 8/2012 | Gupta et al. | |
| 8,237,715 B2 | 8/2012 | Buck et al. | |
| 8,250,483 B2 | 8/2012 | Blomquist | |
| 8,251,907 B2 | 8/2012 | Sterling et al. | |
| 8,257,652 B2 | 9/2012 | Drucker et al. | |
| 8,257,653 B2 | 9/2012 | Drucker et al. | |
| 8,262,616 B2 | 9/2012 | Grant et al. | |
| 8,267,921 B2 | 9/2012 | Yodfat et al. | |
| 8,273,296 B2 | 9/2012 | Drucker et al. | |
| D669,165 S | 10/2012 | Estes et al. | |
| D669,166 S | 10/2012 | Estes et al. | |
| D669,167 S | 10/2012 | Estes et al. | |
| 8,279,226 B2 | 10/2012 | Krieftewirth | |
| 8,310,415 B2 | 11/2012 | Mclaughlin et al. | |
| 8,337,469 B2 | 12/2012 | Eberhart et al. | |
| 8,350,657 B2 | 1/2013 | Derochemont | |
| 8,354,294 B2 | 1/2013 | De et al. | |
| 8,357,091 B2 | 1/2013 | Say et al. | |
| 8,365,065 B2 | 1/2013 | Gejdos et al. | |
| 8,372,005 B2 | 2/2013 | Say et al. | |
| D677,685 S | 3/2013 | Simmons et al. | |
| D682,289 S | 5/2013 | Dijulio et al. | |
| 8,439,834 B2 | 5/2013 | Schmelzeisen-Redeker et al. | |
| 8,449,524 B2 | 5/2013 | Braig et al. | |
| 8,452,359 B2 | 5/2013 | Rebec et al. | |
| D683,738 S | 6/2013 | Wujcik et al. | |
| 8,454,576 B2 | 6/2013 | Mastrototaro et al. | |
| 8,467,980 B2 | 6/2013 | Campbell et al. | |
| 8,478,557 B2 | 7/2013 | Hayter et al. | |
| D687,541 S | 8/2013 | Estes et al. | |
| D688,686 S | 8/2013 | Rhee et al. | |
| 8,514,086 B2 | 8/2013 | Harper et al. | |
| D689,523 S | 9/2013 | Galbraith et al. | |
| D689,874 S | 9/2013 | Brinda et al. | |
| 8,529,838 B2 | 9/2013 | Drucker et al. | |
| 8,529,839 B2 | 9/2013 | Drucker et al. | |
| 8,529,841 B2 | 9/2013 | Drucker et al. | |
| D691,258 S | 10/2013 | Estes et al. | |
| D691,259 S | 10/2013 | Estes et al. | |
| 8,547,239 B2 | 10/2013 | Peatfield et al. | |
| D693,114 S | 11/2013 | Lemanski, Sr. | |
| D693,837 S | 11/2013 | Bouchier | |
| 8,579,815 B2 | 11/2013 | Galley et al. | |
| 8,593,819 B2 | 11/2013 | De Rochemont | |
| D695,757 S | 12/2013 | Ray et al. | |
| 8,597,274 B2 | 12/2013 | Sloan et al. | |
| 8,601,005 B2 | 12/2013 | Bousamra et al. | |
| 8,615,366 B2 | 12/2013 | Galley et al. | |
| D697,204 S | 1/2014 | Maier et al. | |
| 8,622,906 B2 | 1/2014 | Say et al. | |
| 8,622,988 B2 | 1/2014 | Hayter | |
| D699,741 S | 2/2014 | Wantland et al. | |
| 8,657,779 B2 | 2/2014 | Blomquist | |
| D701,879 S | 4/2014 | Foit et al. | |

(56)                    References Cited

U.S. PATENT DOCUMENTS

| | | | |
|---|---|---|---|
| D702,258 | S | 4/2014 | Wantland et al. |
| 8,715,839 | B2 | 5/2014 | De Rochemont |
| 8,719,945 | B2 | 5/2014 | Birtwhistle et al. |
| 8,756,074 | B2 | 6/2014 | Brzustowicz |
| 8,761,940 | B2 | 6/2014 | Long et al. |
| D709,183 | S | 7/2014 | Kemlein |
| 8,774,887 | B2 | 7/2014 | Say et al. |
| D710,879 | S | 8/2014 | Elston et al. |
| 8,810,394 | B2 | 8/2014 | Kalpin |
| 8,816,862 | B2 | 8/2014 | Harper et al. |
| 8,839,106 | B2 | 9/2014 | Lee et al. |
| D714,816 | S | 10/2014 | Varon |
| D714,822 | S | 10/2014 | Capua et al. |
| D715,315 | S | 10/2014 | Wood |
| D715,815 | S | 10/2014 | Bortman et al. |
| D715,835 | S | 10/2014 | Montgomery et al. |
| D717,822 | S | 11/2014 | Brotman et al. |
| D717,830 | S | 11/2014 | Brinda et al. |
| D718,438 | S | 11/2014 | Davis et al. |
| 8,895,315 | B2 | 11/2014 | Batman et al. |
| D718,779 | S | 12/2014 | Hang et al. |
| D719,186 | S | 12/2014 | Kim |
| D720,366 | S | 12/2014 | Hiltunen et al. |
| D720,765 | S | 1/2015 | Xie et al. |
| 8,939,935 | B2 | 1/2015 | O'Connor et al. |
| 8,961,465 | B2 | 2/2015 | Blomquist |
| D726,760 | S | 4/2015 | Yokota et al. |
| D727,336 | S | 4/2015 | Allison et al. |
| D727,928 | S | 4/2015 | Allison et al. |
| 9,008,803 | B2 | 4/2015 | Blomquist |
| D730,378 | S | 5/2015 | Xiong et al. |
| 9,022,996 | B2 | 5/2015 | Eberhart et al. |
| 9,033,877 | B2 | 5/2015 | Werner et al. |
| 9,041,730 | B2 | 5/2015 | Johnson et al. |
| D733,175 | S | 6/2015 | Bae |
| D733,179 | S | 6/2015 | Kwon |
| 9,050,409 | B2 | 6/2015 | Haueter et al. |
| 9,061,097 | B2 | 6/2015 | Holt et al. |
| D734,356 | S | 7/2015 | Xiong et al. |
| 9,072,477 | B2 | 7/2015 | Say et al. |
| 9,076,107 | B2 | 7/2015 | Cameron et al. |
| D736,792 | S | 8/2015 | Brinda et al. |
| D736,811 | S | 8/2015 | Teichner et al. |
| D737,278 | S | 8/2015 | Shin et al. |
| D737,305 | S | 8/2015 | Scazafavo et al. |
| D737,831 | S | 9/2015 | Lee |
| D737,832 | S | 9/2015 | Lim et al. |
| D738,901 | S | 9/2015 | Amin |
| D738,907 | S | 9/2015 | Cabrera-Cordon et al. |
| D738,913 | S | 9/2015 | Cabrera-Cordon et al. |
| D738,914 | S | 9/2015 | Torres et al. |
| 9,134,823 | B2 | 9/2015 | Grant et al. |
| 9,136,939 | B2 | 9/2015 | Galley et al. |
| D740,301 | S | 10/2015 | Soegiono et al. |
| D740,308 | S | 10/2015 | Kim et al. |
| D740,311 | S | 10/2015 | Drozd et al. |
| D741,354 | S | 10/2015 | Lee et al. |
| D741,359 | S | 10/2015 | Ji-Hye et al. |
| 9,159,148 | B2 | 10/2015 | Boyer et al. |
| 9,171,343 | B1 | 10/2015 | Fischell et al. |
| D743,431 | S | 11/2015 | Pal et al. |
| D743,435 | S | 11/2015 | Herold et al. |
| D743,991 | S | 11/2015 | Pal et al. |
| 9,180,224 | B2 | 11/2015 | Moseley et al. |
| 9,180,244 | B2 | 11/2015 | Anderson et al. |
| 9,186,113 | B2 | 11/2015 | Harper et al. |
| 9,192,716 | B2 | 11/2015 | Jugl et al. |
| D744,505 | S | 12/2015 | Wilberding et al. |
| D744,514 | S | 12/2015 | Shin et al. |
| D744,517 | S | 12/2015 | Pal et al. |
| D745,032 | S | 12/2015 | Pal et al. |
| D745,034 | S | 12/2015 | Pal et al. |
| D745,035 | S | 12/2015 | Pal et al. |
| D745,050 | S | 12/2015 | Kwon |
| 9,198,623 | B2 | 12/2015 | Fern et al. |
| D746,827 | S | 1/2016 | Jung et al. |
| D746,828 | S | 1/2016 | Arai et al. |
| D747,352 | S | 1/2016 | Lee et al. |
| 9,233,204 | B2 | 1/2016 | Booth et al. |
| D749,097 | S | 2/2016 | Zou et al. |
| D749,118 | S | 2/2016 | Wang |
| D751,100 | S | 3/2016 | Lindn et al. |
| D751,585 | S | 3/2016 | Kaufthal et al. |
| D751,586 | S | 3/2016 | Kaufthal et al. |
| D752,604 | S | 3/2016 | Zhang |
| D752,736 | S | 3/2016 | Chandrasenan et al. |
| D753,134 | S | 4/2016 | Vazquez |
| D754,718 | S | 4/2016 | Zhou |
| D755,193 | S | 5/2016 | Sun et al. |
| D755,799 | S | 5/2016 | Finnis et al. |
| D755,820 | S | 5/2016 | Wang |
| D755,830 | S | 5/2016 | Chaudhri et al. |
| D756,387 | S | 5/2016 | Chang et al. |
| D757,026 | S | 5/2016 | Lim et al. |
| D757,032 | S | 5/2016 | Sabia et al. |
| D757,035 | S | 5/2016 | Raskin et al. |
| D757,047 | S | 5/2016 | Cornwell et al. |
| 9,336,355 | B2 | 5/2016 | Ljuhs et al. |
| D758,391 | S | 6/2016 | Suarez |
| D758,422 | S | 6/2016 | Zhao |
| D759,032 | S | 6/2016 | Amin et al. |
| D759,078 | S | 6/2016 | Iwamoto |
| D759,678 | S | 6/2016 | Jung et al. |
| D759,687 | S | 6/2016 | Chang et al. |
| D761,812 | S | 7/2016 | Motamedi |
| D763,308 | S | 8/2016 | Wang et al. |
| D763,860 | S | 8/2016 | Sunshine et al. |
| D763,868 | S | 8/2016 | Lee et al. |
| D765,110 | S | 8/2016 | Liang |
| D765,124 | S | 8/2016 | Minks-Brown et al. |
| 9,402,950 | B2 | 8/2016 | Dilanni et al. |
| D765,707 | S | 9/2016 | Gomez |
| D766,286 | S | 9/2016 | Lee et al. |
| D766,424 | S | 9/2016 | Anderson et al. |
| D767,586 | S | 9/2016 | Kwon et al. |
| D768,144 | S | 10/2016 | Kim et al. |
| D768,154 | S | 10/2016 | Kim et al. |
| D768,188 | S | 10/2016 | Li et al. |
| D768,660 | S | 10/2016 | Wielgosz |
| D768,685 | S | 10/2016 | Lee et al. |
| D768,687 | S | 10/2016 | Bae et al. |
| D769,315 | S | 10/2016 | Scotti |
| D769,322 | S | 10/2016 | Rajeswaran et al. |
| D770,507 | S | 11/2016 | Umezawa et al. |
| D770,515 | S | 11/2016 | Cho et al. |
| D771,073 | S | 11/2016 | Choi et al. |
| D771,076 | S | 11/2016 | Butcher et al. |
| D771,690 | S | 11/2016 | Yin et al. |
| D772,911 | S | 11/2016 | Lee et al. |
| D772,924 | S | 11/2016 | Begin et al. |
| 9,486,571 | B2 | 11/2016 | Rosinko |
| 9,498,164 | B2 | 11/2016 | Johnson et al. |
| 9,498,165 | B2 | 11/2016 | Johnson et al. |
| 9,504,430 | B2 | 11/2016 | Johnson et al. |
| D773,531 | S | 12/2016 | Toth et al. |
| D775,184 | S | 12/2016 | Song et al. |
| D775,196 | S | 12/2016 | Huang et al. |
| 9,520,649 | B2 | 12/2016 | De Rochemont |
| D775,658 | S | 1/2017 | Luo et al. |
| D776,126 | S | 1/2017 | Lai et al. |
| D776,253 | S | 1/2017 | Li |
| D776,687 | S | 1/2017 | Wick et al. |
| D777,191 | S | 1/2017 | Polimeni |
| D777,758 | S | 1/2017 | Kisselev et al. |
| D777,906 | S | 1/2017 | Anderson et al. |
| 9,579,456 | B2 | 2/2017 | Budiman et al. |
| D781,305 | S | 3/2017 | Lau |
| D781,323 | S | 3/2017 | Green et al. |
| D781,781 | S | 3/2017 | Schimmoeller, Jr. |
| D781,877 | S | 3/2017 | Ko et al. |
| D781,878 | S | 3/2017 | Butcher et al. |
| D781,879 | S | 3/2017 | Butcher et al. |
| D781,903 | S | 3/2017 | Reichle et al. |
| D781,905 | S | 3/2017 | Nakaguchi et al. |

(56)                    References Cited

U.S. PATENT DOCUMENTS

| | | | |
|---|---|---|---|
| D781,908 S | 3/2017 | Bhandari et al. |
| D782,506 S | 3/2017 | Kim et al. |
| D783,672 S | 4/2017 | Rajasankar et al. |
| D785,010 S | 4/2017 | Bachman et al. |
| D785,656 S | 5/2017 | Bramer et al. |
| D786,266 S | 5/2017 | Van et al. |
| D786,270 S | 5/2017 | Barry et al. |
| D786,278 S | 5/2017 | Motamedi |
| D786,898 S | 5/2017 | Hall |
| D788,126 S | 5/2017 | Evnin et al. |
| D788,145 S | 5/2017 | Sullivan et al. |
| 9,656,017 B2 | 5/2017 | Greene |
| D788,621 S | 6/2017 | Shallice et al. |
| D788,652 S | 6/2017 | Mutsuro et al. |
| D789,402 S | 6/2017 | Dye et al. |
| D789,967 S | 6/2017 | Kaplan et al. |
| D789,982 S | 6/2017 | Christiana et al. |
| D790,560 S | 6/2017 | Inose et al. |
| D791,781 S | 7/2017 | Donarski et al. |
| D791,805 S | 7/2017 | Segars |
| D791,812 S | 7/2017 | Bistoni et al. |
| 9,707,336 B2 | 7/2017 | Dang et al. |
| D793,412 S | 8/2017 | Chaudhri et al. |
| D795,284 S | 8/2017 | Miller et al. |
| D795,886 S | 8/2017 | Ng et al. |
| D795,891 S | 8/2017 | Kohan et al. |
| D795,900 S | 8/2017 | Bischoff et al. |
| D795,906 S | 8/2017 | Butrick |
| D795,927 S | 8/2017 | Bischoff et al. |
| 9,717,849 B2 | 8/2017 | Mhatre et al. |
| 9,743,224 B2 | 8/2017 | San et al. |
| D796,530 S | 9/2017 | Mcmillan et al. |
| D796,540 S | 9/2017 | Mclean et al. |
| D797,116 S | 9/2017 | Chapman et al. |
| D797,763 S | 9/2017 | Kim et al. |
| D797,771 S | 9/2017 | Caporal et al. |
| D797,774 S | 9/2017 | Park et al. |
| D797,797 S | 9/2017 | Gandhi et al. |
| D798,310 S | 9/2017 | Golden et al. |
| D798,311 S | 9/2017 | Golden et al. |
| D799,536 S | 10/2017 | Eder |
| D800,757 S | 10/2017 | Mullen et al. |
| D800,765 S | 10/2017 | Stoksik |
| D800,769 S | 10/2017 | Hennessy et al. |
| D801,383 S | 10/2017 | Park et al. |
| D801,519 S | 10/2017 | Sabin et al. |
| D802,011 S | 11/2017 | Friedman et al. |
| D802,088 S | 11/2017 | Bos et al. |
| D803,232 S | 11/2017 | Leigh et al. |
| D803,242 S | 11/2017 | Mizono et al. |
| D804,502 S | 12/2017 | Amini et al. |
| D805,525 S | 12/2017 | Dascola et al. |
| 9,833,199 B2 | 12/2017 | Johnson et al. |
| D806,716 S | 1/2018 | Pahwa et al. |
| D806,748 S | 1/2018 | Van et al. |
| D806,749 S | 1/2018 | Van et al. |
| D806,750 S | 1/2018 | Van et al. |
| D807,376 S | 1/2018 | Mizono et al. |
| D807,400 S | 1/2018 | Lagreca |
| D807,910 S | 1/2018 | Graham et al. |
| D807,918 S | 1/2018 | Cohen et al. |
| D807,919 S | 1/2018 | Cohen et al. |
| D808,423 S | 1/2018 | Jiang et al. |
| D808,974 S | 1/2018 | Chiappone et al. |
| D808,983 S | 1/2018 | Narinedhat et al. |
| D809,134 S | 1/2018 | Crothall |
| 9,857,090 B2 | 1/2018 | Golden et al. |
| 9,878,097 B2 | 1/2018 | Estes |
| D810,116 S | 2/2018 | Mclean et al. |
| D810,771 S | 2/2018 | Gandhi et al. |
| 9,907,515 B2 | 3/2018 | Doyle et al. |
| D815,131 S | 4/2018 | Thompson et al. |
| D816,090 S | 4/2018 | Stonecipher et al. |
| 9,931,454 B2 | 4/2018 | Lo et al. |
| D817,339 S | 5/2018 | Nanjappan et al. |
| D818,491 S | 5/2018 | Timmer et al. |
| D819,057 S | 5/2018 | Huang |
| D819,059 S | 5/2018 | Julia |
| 9,980,140 B1 | 5/2018 | Spencer et al. |
| 9,984,773 B2 | 5/2018 | Gondhalekar et al. |
| D820,311 S | 6/2018 | Cabrera et al. |
| D820,862 S | 6/2018 | Alfonzo et al. |
| D822,034 S | 7/2018 | Clymer et al. |
| D822,677 S | 7/2018 | Weaver et al. |
| D822,684 S | 7/2018 | Clausen-Stuck et al. |
| D822,692 S | 7/2018 | Loychik et al. |
| D823,862 S | 7/2018 | Chung et al. |
| D824,400 S | 7/2018 | Chang et al. |
| D824,951 S | 8/2018 | Kolbrener et al. |
| D826,956 S | 8/2018 | Pillalamarri et al. |
| D826,957 S | 8/2018 | Pillalamarri et al. |
| D828,381 S | 9/2018 | Lee et al. |
| D829,732 S | 10/2018 | Jeffrey et al. |
| D830,374 S | 10/2018 | Leonard et al. |
| D830,384 S | 10/2018 | Lepine et al. |
| D830,385 S | 10/2018 | Lepine et al. |
| D830,407 S | 10/2018 | Kisielius et al. |
| D831,033 S | 10/2018 | Leonard et al. |
| D833,469 S | 11/2018 | Coleman et al. |
| D834,601 S | 11/2018 | Felt |
| D835,132 S | 12/2018 | Ito et al. |
| D835,145 S | 12/2018 | Cashner et al. |
| D835,147 S | 12/2018 | Kisielius et al. |
| D835,651 S | 12/2018 | Bao |
| D835,666 S | 12/2018 | Saleh et al. |
| D836,123 S | 12/2018 | Pillalamarri et al. |
| 10,154,804 B2 | 12/2018 | Steil et al. |
| D837,807 S | 1/2019 | Baber et al. |
| D838,731 S | 1/2019 | Pillalamarri et al. |
| 10,165,986 B2 | 1/2019 | Johnson et al. |
| D840,418 S | 2/2019 | Saad et al. |
| D840,419 S | 2/2019 | Saad et al. |
| D844,022 S | 3/2019 | Amin |
| D845,317 S | 4/2019 | Wellmeier et al. |
| 10,248,839 B2 | 4/2019 | Levy et al. |
| 10,265,030 B2 | 4/2019 | Johnson et al. |
| D848,459 S | 5/2019 | Li |
| 10,278,650 B2 | 5/2019 | Johnson et al. |
| D851,099 S | 6/2019 | Uppala et al. |
| D851,658 S | 6/2019 | Pillalamarri et al. |
| 10,335,464 B1 | 7/2019 | Michelich et al. |
| 10,426,896 B2 | 10/2019 | Desborough et al. |
| D865,795 S | 11/2019 | Koo |
| D872,746 S | 1/2020 | Laborde |
| D874,471 S | 2/2020 | Pillalamarri et al. |
| D875,114 S | 2/2020 | Clediere |
| D880,498 S | 4/2020 | Shahidi et al. |
| D888,070 S | 6/2020 | Yusupov et al. |
| 10,737,024 B2 | 8/2020 | Schmid |
| D904,426 S | 12/2020 | Paul |
| D911,353 S | 2/2021 | Sanchez et al. |
| D914,031 S | 3/2021 | Ding et al. |
| D916,729 S | 4/2021 | Gabriel et al. |
| D916,870 S | 4/2021 | Hemsley |
| D916,878 S | 4/2021 | Kim et al. |
| D918,261 S | 5/2021 | Ramamurthy et al. |
| D920,351 S | 5/2021 | Zhang |
| D923,033 S | 6/2021 | Smith et al. |
| D927,533 S | 8/2021 | Clymer |
| D938,447 S | 12/2021 | Holland |
| 11,197,964 B2 | 12/2021 | Sjolund et al. |
| 11,260,169 B2 | 3/2022 | Estes |
| D954,078 S | 6/2022 | Rahate et al. |
| 11,389,088 B2 * | 7/2022 | Desborough .......... A61B 5/744 |
| 2001/0034023 A1 | 10/2001 | Stanton et al. |
| 2001/0034502 A1 | 10/2001 | Moberg et al. |
| 2001/0041869 A1 | 11/2001 | Causey et al. |
| 2001/0048969 A1 | 12/2001 | Constantino et al. |
| 2001/0051377 A1 | 12/2001 | Hammer et al. |
| 2001/0056258 A1 | 12/2001 | Evans |
| 2001/0056262 A1 | 12/2001 | Cabiri et al. |
| 2002/0004651 A1 | 1/2002 | Ljunggreen et al. |
| 2002/0007154 A1 | 1/2002 | Hansen et al. |
| 2002/0010401 A1 | 1/2002 | Bushmakin et al. |

(56)  References Cited

U.S. PATENT DOCUMENTS

| | | |
|---|---|---|
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0047768 A1 | 4/2002 | Duffy |
| 2002/0070983 A1 | 6/2002 | Kozub et al. |
| 2002/0091358 A1 | 7/2002 | Klitmose |
| 2002/0126036 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2002/0173769 A1 | 11/2002 | Gray et al. |
| 2002/0177810 A1 | 11/2002 | Reilly et al. |
| 2002/0190818 A1 | 12/2002 | Endou et al. |
| 2003/0023148 A1 | 1/2003 | Lorenz et al. |
| 2003/0034124 A1 | 2/2003 | Sugaya et al. |
| 2003/0040715 A1 | 2/2003 | D'Antonio et al. |
| 2003/0055380 A1 | 3/2003 | Flaherty |
| 2003/0060692 A1 | 3/2003 | L. Ruchti et al. |
| 2003/0065308 A1 | 4/2003 | Lebel et al. |
| 2003/0086073 A1 | 5/2003 | Braig et al. |
| 2003/0088238 A1 | 5/2003 | Poulsen et al. |
| 2003/0100040 A1 | 5/2003 | Bonnecaze et al. |
| 2003/0122647 A1 | 7/2003 | Ou |
| 2003/0135388 A1 | 7/2003 | Martucci et al. |
| 2003/0144582 A1 | 7/2003 | Cohen et al. |
| 2003/0148024 A1 | 8/2003 | Kodas et al. |
| 2003/0163097 A1 | 8/2003 | Fleury et al. |
| 2003/0167035 A1 | 9/2003 | Flaherty et al. |
| 2003/0170436 A1 | 9/2003 | Sumi et al. |
| 2003/0175806 A1 | 9/2003 | Rule et al. |
| 2003/0195404 A1 | 10/2003 | Knobbe et al. |
| 2003/0198558 A1 | 10/2003 | Nason et al. |
| 2003/0199825 A1 | 10/2003 | Flaherty |
| 2003/0208113 A1 | 11/2003 | Mault et al. |
| 2003/0212379 A1 | 11/2003 | Bylund et al. |
| 2003/0216627 A1 | 11/2003 | Lorenz et al. |
| 2003/0216683 A1 | 11/2003 | Shekalim |
| 2003/0220605 A1 | 11/2003 | Bowman et al. |
| 2003/0221621 A1 | 12/2003 | Pokharna et al. |
| 2004/0010207 A1 | 1/2004 | Flaherty et al. |
| 2004/0019325 A1 | 1/2004 | Shekalim |
| 2004/0045879 A1 | 3/2004 | Shults et al. |
| 2004/0051368 A1 | 3/2004 | Caputo et al. |
| 2004/0064088 A1 | 4/2004 | Gorman et al. |
| 2004/0064096 A1 | 4/2004 | Flaherty et al. |
| 2004/0064259 A1 | 4/2004 | Haaland et al. |
| 2004/0068224 A1 | 4/2004 | Couvillon et al. |
| 2004/0069004 A1 | 4/2004 | Gist et al. |
| 2004/0069044 A1 | 4/2004 | Lavi et al. |
| 2004/0078028 A1 | 4/2004 | Flaherty et al. |
| 2004/0087894 A1 | 5/2004 | Flaherty |
| 2004/0087904 A1 | 5/2004 | Langley et al. |
| 2004/0092865 A1 | 5/2004 | Flaherty et al. |
| 2004/0092878 A1 | 5/2004 | Flaherty |
| 2004/0093331 A1 | 5/2004 | Garner et al. |
| 2004/0097796 A1 | 5/2004 | Berman et al. |
| 2004/0116847 A1 | 6/2004 | Wall |
| 2004/0116866 A1 | 6/2004 | Gorman et al. |
| 2004/0122353 A1 | 6/2004 | Shahmirian et al. |
| 2004/0127844 A1 | 7/2004 | Flaherty |
| 2004/0133166 A1 | 7/2004 | Moberg et al. |
| 2004/0147034 A1 | 7/2004 | Gore et al. |
| 2004/0153032 A1 | 8/2004 | Garribotto et al. |
| 2004/0153257 A1 | 8/2004 | Munk |
| 2004/0171983 A1 | 9/2004 | Sparks et al. |
| 2004/0176727 A1 | 9/2004 | Shekalim |
| 2004/0203357 A1 | 10/2004 | Nassimi |
| 2004/0204673 A1 | 10/2004 | Flaherty |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0220551 A1 | 11/2004 | Flaherty et al. |
| 2004/0235446 A1 | 11/2004 | Flaherty et al. |
| 2004/0241736 A1 | 12/2004 | Hendee et al. |
| 2004/0249308 A1 | 12/2004 | Forssell |
| 2004/0260233 A1 | 12/2004 | Garibotto et al. |
| 2005/0003470 A1 | 1/2005 | Nelson et al. |
| 2005/0020980 A1 | 1/2005 | Inoue et al. |
| 2005/0021005 A1 | 1/2005 | Flaherty et al. |
| 2005/0022274 A1 | 1/2005 | Campbell et al. |
| 2005/0037482 A1* | 2/2005 | Braig ................ A61B 5/14532<br>435/287.1 |
| 2005/0049179 A1 | 3/2005 | Davidson et al. |
| 2005/0065464 A1 | 3/2005 | Talbot et al. |
| 2005/0065760 A1 | 3/2005 | Murtfeldt et al. |
| 2005/0075624 A1 | 4/2005 | Miesel |
| 2005/0090808 A1 | 4/2005 | Malave et al. |
| 2005/0090851 A1 | 4/2005 | Devlin |
| 2005/0095063 A1 | 5/2005 | Fathallah et al. |
| 2005/0105095 A1 | 5/2005 | Pesach et al. |
| 2005/0134609 A1 | 6/2005 | Yu |
| 2005/0137573 A1 | 6/2005 | Mclaughlin |
| 2005/0159656 A1 | 7/2005 | Hockersmith et al. |
| 2005/0160858 A1 | 7/2005 | Mernoe |
| 2005/0171512 A1 | 8/2005 | Flaherty |
| 2005/0182306 A1 | 8/2005 | Sloan |
| 2005/0182366 A1 | 8/2005 | Vogt et al. |
| 2005/0192494 A1 | 9/2005 | Ginsberg |
| 2005/0192557 A1 | 9/2005 | Brauker et al. |
| 2005/0192561 A1 | 9/2005 | Mernoe |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0209515 A1 | 9/2005 | Hockersmith et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | Diianni et al. |
| 2005/0245878 A1 | 11/2005 | Mernoe et al. |
| 2005/0251097 A1 | 11/2005 | Mernoe |
| 2005/0261660 A1 | 11/2005 | Choi |
| 2005/0262451 A1 | 11/2005 | Remignanti et al. |
| 2005/0267402 A1 | 12/2005 | Stewart et al. |
| 2005/0273059 A1 | 12/2005 | Mernoe et al. |
| 2005/0277912 A1 | 12/2005 | John |
| 2006/0009727 A1 | 1/2006 | O'Mahony et al. |
| 2006/0041229 A1 | 2/2006 | Garibotto et al. |
| 2006/0064053 A1 | 3/2006 | Bollish et al. |
| 2006/0069382 A1 | 3/2006 | Pedersen |
| 2006/0074381 A1 | 4/2006 | Malave et al. |
| 2006/0079765 A1 | 4/2006 | Neer et al. |
| 2006/0086994 A1 | 4/2006 | Viefers et al. |
| 2006/0095014 A1 | 5/2006 | Ethelfeld |
| 2006/0134323 A1 | 6/2006 | O'Brien |
| 2006/0134491 A1 | 6/2006 | Hilchenko et al. |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0167350 A1 | 7/2006 | Monfre et al. |
| 2006/0178633 A1 | 8/2006 | Garibotto et al. |
| 2006/0184119 A1 | 8/2006 | Remde et al. |
| 2006/0189925 A1 | 8/2006 | Gable et al. |
| 2006/0189926 A1 | 8/2006 | Hall et al. |
| 2006/0200070 A1 | 9/2006 | Callicoat et al. |
| 2006/0200073 A1 | 9/2006 | Radmer et al. |
| 2006/0204535 A1 | 9/2006 | Johnson |
| 2006/0206054 A1 | 9/2006 | Shekalim |
| 2006/0229531 A1 | 10/2006 | Goldberger et al. |
| 2006/0247581 A1 | 11/2006 | Pedersen et al. |
| 2006/0253085 A1 | 11/2006 | Geismar et al. |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0083160 A1 | 4/2007 | Hall et al. |
| 2007/0088271 A1 | 4/2007 | Richards |
| 2007/0100635 A1 | 5/2007 | Mahajan et al. |

US 12,653,426 B2

Page 10

(56) References Cited

U.S. PATENT DOCUMENTS

| 2007/0106218 | A1 | 5/2007 | Yodfat et al. |
| 2007/0116601 | A1 | 5/2007 | Patton |
| 2007/0118405 | A1 | 5/2007 | Campbell et al. |
| 2007/0124002 | A1 | 5/2007 | Estes et al. |
| 2007/0129690 | A1 | 6/2007 | Rosenblatt et al. |
| 2007/0142720 | A1 | 6/2007 | Ridder et al. |
| 2007/0156092 | A1 | 7/2007 | Estes et al. |
| 2007/0166453 | A1 | 7/2007 | Van et al. |
| 2007/0167905 | A1 | 7/2007 | Estes et al. |
| 2007/0167912 | A1 | 7/2007 | Causey et al. |
| 2007/0173974 | A1 | 7/2007 | Lin |
| 2007/0179352 | A1 | 8/2007 | Randlov et al. |
| 2007/0179444 | A1 | 8/2007 | Causey et al. |
| 2007/0191716 | A1 | 8/2007 | Goldberger et al. |
| 2007/0197163 | A1 | 8/2007 | Robertson |
| 2007/0225675 | A1 | 9/2007 | Robinson et al. |
| 2007/0239116 | A1 | 10/2007 | Follman et al. |
| 2007/0244381 | A1 | 10/2007 | Robinson et al. |
| 2007/0249007 | A1 | 10/2007 | Rosero |
| 2007/0259768 | A1 | 11/2007 | Kear et al. |
| 2007/0264707 | A1 | 11/2007 | Liederman et al. |
| 2007/0282269 | A1 | 12/2007 | Carter et al. |
| 2007/0293843 | A1 | 12/2007 | Ireland et al. |
| 2008/0033254 | A1 | 2/2008 | Kamath et al. |
| 2008/0033272 | A1 | 2/2008 | Gough et al. |
| 2008/0033320 | A1 | 2/2008 | Racchini et al. |
| 2008/0051716 | A1 | 2/2008 | Stutz |
| 2008/0051738 | A1 | 2/2008 | Griffin |
| 2008/0051764 | A1 | 2/2008 | Dent et al. |
| 2008/0058625 | A1 | 3/2008 | Mcgarraugh et al. |
| 2008/0065050 | A1 | 3/2008 | Sparks et al. |
| 2008/0071157 | A1 | 3/2008 | Mcgarraugh et al. |
| 2008/0071158 | A1 | 3/2008 | Mcgarraugh et al. |
| 2008/0078400 | A1 | 4/2008 | Martens et al. |
| 2008/0097289 | A1 | 4/2008 | Steil et al. |
| 2008/0097381 | A1 | 4/2008 | Moberg et al. |
| 2008/0114304 | A1 | 5/2008 | Nalesso et al. |
| 2008/0119705 | A1 | 5/2008 | Patel et al. |
| 2008/0132880 | A1 | 6/2008 | Buchman |
| 2008/0160492 | A1 | 7/2008 | Campbell et al. |
| 2008/0172026 | A1 | 7/2008 | Blomquist |
| 2008/0172028 | A1 | 7/2008 | Blomquist |
| 2008/0188796 | A1 | 8/2008 | Steil et al. |
| 2008/0200838 | A1 | 8/2008 | Goldberger et al. |
| 2008/0206067 | A1 | 8/2008 | De et al. |
| 2008/0208627 | A1 | 8/2008 | Skyggebjerg |
| 2008/0214919 | A1 | 9/2008 | Harmon et al. |
| 2008/0228056 | A1 | 9/2008 | Blomquist et al. |
| 2008/0249386 | A1 | 10/2008 | Besterman et al. |
| 2008/0269585 | A1 | 10/2008 | Ginsberg |
| 2008/0269714 | A1 | 10/2008 | Mastrototaro et al. |
| 2008/0269723 | A1 | 10/2008 | Mastrototaro et al. |
| 2008/0287755 | A1 | 11/2008 | Sass et al. |
| 2008/0287906 | A1 | 11/2008 | Burkholz et al. |
| 2008/0294094 | A1 | 11/2008 | Mhatre et al. |
| 2008/0294108 | A1 | 11/2008 | Briones et al. |
| 2008/0294109 | A1 | 11/2008 | Estes et al. |
| 2008/0294142 | A1 | 11/2008 | Patel et al. |
| 2008/0300572 | A1 | 12/2008 | Rankers et al. |
| 2008/0319383 | A1 | 12/2008 | Byland et al. |
| 2009/0006061 | A1 | 1/2009 | Thukral et al. |
| 2009/0018406 | A1 | 1/2009 | Yodfat et al. |
| 2009/0030398 | A1 | 1/2009 | Yodfat et al. |
| 2009/0036753 | A1 | 2/2009 | King |
| 2009/0043240 | A1 | 2/2009 | Robinson et al. |
| 2009/0054753 | A1 | 2/2009 | Robinson et al. |
| 2009/0067989 | A1 | 3/2009 | Estes et al. |
| 2009/0069743 | A1 | 3/2009 | Krishnamoorthy et al. |
| 2009/0069745 | A1 | 3/2009 | Estes et al. |
| 2009/0069746 | A1 | 3/2009 | Miller et al. |
| 2009/0069749 | A1 | 3/2009 | Miller et al. |
| 2009/0069784 | A1 | 3/2009 | Estes et al. |
| 2009/0069785 | A1 | 3/2009 | Miller et al. |
| 2009/0069787 | A1 | 3/2009 | Estes et al. |
| 2009/0099521 | A1 | 4/2009 | Gravesen et al. |
| 2009/0099523 | A1 | 4/2009 | Grant et al. |
| 2009/0113295 | A1* | 4/2009 | Halpern ............ A61B 5/14532 715/273 |
| 2009/0156922 | A1 | 6/2009 | Goldberger et al. |
| 2009/0156924 | A1 | 6/2009 | Shariati et al. |
| 2009/0156990 | A1 | 6/2009 | Wenger et al. |
| 2009/0163781 | A1 | 6/2009 | Say et al. |
| 2009/0198350 | A1 | 8/2009 | Thiele |
| 2009/0212966 | A1 | 8/2009 | Panduro |
| 2009/0221890 | A1 | 9/2009 | Saffer et al. |
| 2009/0228214 | A1 | 9/2009 | Say et al. |
| 2009/0292247 | A1 | 11/2009 | Basso et al. |
| 2009/0318791 | A1 | 12/2009 | Kaastrup |
| 2009/0326343 | A1 | 12/2009 | Gable et al. |
| 2009/0326472 | A1 | 12/2009 | Carter et al. |
| 2010/0010330 | A1 | 1/2010 | Rankers et al. |
| 2010/0017141 | A1 | 1/2010 | Campbell et al. |
| 2010/0036326 | A1 | 2/2010 | Matusch |
| 2010/0057042 | A1 | 3/2010 | Hayter |
| 2010/0075353 | A1 | 3/2010 | Heaton |
| 2010/0077198 | A1 | 3/2010 | Buck et al. |
| 2010/0114026 | A1 | 5/2010 | Karratt et al. |
| 2010/0121170 | A1 | 5/2010 | Rule |
| 2010/0137784 | A1 | 6/2010 | Cefai et al. |
| 2010/0145272 | A1 | 6/2010 | Cefai et al. |
| 2010/0152658 | A1 | 6/2010 | Hanson et al. |
| 2010/0174228 | A1 | 7/2010 | Buckingham et al. |
| 2010/0185183 | A1 | 7/2010 | Alme et al. |
| 2010/0211003 | A1 | 8/2010 | Sundar et al. |
| 2010/0228110 | A1 | 9/2010 | Tsoukalis |
| 2010/0241066 | A1 | 9/2010 | Hansen et al. |
| 2010/0262117 | A1 | 10/2010 | Magni et al. |
| 2010/0262434 | A1 | 10/2010 | Shaya |
| 2010/0280329 | A1 | 11/2010 | Pedersen et al. |
| 2010/0298765 | A1 | 11/2010 | Budiman et al. |
| 2010/0305965 | A1 | 12/2010 | Benjamin et al. |
| 2011/0009846 | A1 | 1/2011 | Istoc et al. |
| 2011/0021584 | A1 | 1/2011 | Berggren et al. |
| 2011/0028817 | A1 | 2/2011 | Jin et al. |
| 2011/0040247 | A1 | 2/2011 | Mandro et al. |
| 2011/0049394 | A1 | 3/2011 | De Rochemont |
| 2011/0054390 | A1 | 3/2011 | Searle et al. |
| 2011/0054399 | A1 | 3/2011 | Chong et al. |
| 2011/0065224 | A1 | 3/2011 | Bollman et al. |
| 2011/0071765 | A1 | 3/2011 | Yodfat et al. |
| 2011/0124996 | A1 | 5/2011 | Reinke et al. |
| 2011/0144586 | A1 | 6/2011 | Michaud et al. |
| 2011/0160555 | A1 | 6/2011 | Reifman et al. |
| 2011/0160652 | A1 | 6/2011 | Yodfat et al. |
| 2011/0178472 | A1 | 7/2011 | Cabiri |
| 2011/0190694 | A1 | 8/2011 | Lanier et al. |
| 2011/0201911 | A1* | 8/2011 | Johnson ............... A61B 5/7475 345/173 |
| 2011/0202005 | A1 | 8/2011 | Yodfat et al. |
| 2011/0218495 | A1 | 9/2011 | Remde |
| 2011/0230833 | A1 | 9/2011 | Landman et al. |
| 2011/0251509 | A1 | 10/2011 | Beyhan et al. |
| 2011/0313680 | A1 | 12/2011 | Doyle et al. |
| 2011/0316562 | A1 | 12/2011 | Cefai et al. |
| 2012/0003935 | A1 | 1/2012 | Lydon et al. |
| 2012/0022496 | A1 | 1/2012 | Causey et al. |
| 2012/0030393 | A1 | 2/2012 | Ganesh et al. |
| 2012/0053556 | A1 | 3/2012 | Lee |
| 2012/0053560 | A1 | 3/2012 | Kawamura |
| 2012/0078067 | A1 | 3/2012 | Kovatchev et al. |
| 2012/0078161 | A1 | 3/2012 | Masterson et al. |
| 2012/0078181 | A1 | 3/2012 | Smith et al. |
| 2012/0101451 | A1 | 4/2012 | Boit et al. |
| 2012/0123234 | A1 | 5/2012 | Atlas et al. |
| 2012/0124521 | A1 | 5/2012 | Guo |
| 2012/0150446 | A1 | 6/2012 | Chang et al. |
| 2012/0190955 | A1 | 7/2012 | Rao et al. |
| 2012/0203085 | A1 | 8/2012 | Rebec |
| 2012/0203166 | A1* | 8/2012 | Riback ................ A61M 5/1723 702/19 |
| 2012/0203178 | A1 | 8/2012 | Tverskoy |
| 2012/0203467 | A1 | 8/2012 | Kamath et al. |
| 2012/0209091 | A1 | 8/2012 | Riback et al. |
| 2012/0209099 | A1 | 8/2012 | Ljuhs et al. |

(56)                    References Cited

U.S. PATENT DOCUMENTS

| | | |
|---|---|---|
| 2012/0215086 A1 | 8/2012 | Kamath et al. |
| 2012/0215087 A1 | 8/2012 | Cobelli et al. |
| 2012/0215201 A1 | 8/2012 | Brauker et al. |
| 2012/0215496 A1 | 8/2012 | Kamath et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0238999 A1 | 9/2012 | Estes et al. |
| 2012/0245855 A1 | 9/2012 | Kamath et al. |
| 2012/0250449 A1 | 10/2012 | Nakano |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2012/0323100 A1 | 12/2012 | Kamath et al. |
| 2012/0330270 A1 | 12/2012 | Colton |
| 2013/0030358 A1 | 1/2013 | Yodfat et al. |
| 2013/0158503 A1 | 6/2013 | Kanderian et al. |
| 2013/0172695 A1 | 7/2013 | Nielsen et al. |
| 2013/0172710 A1 | 7/2013 | Mears et al. |
| 2013/0178791 A1 | 7/2013 | Javitt |
| 2013/0231642 A1 | 9/2013 | Doyle et al. |
| 2013/0245545 A1 | 9/2013 | Arnold et al. |
| 2013/0253472 A1 | 9/2013 | Cabiri |
| 2013/0261406 A1 | 10/2013 | Rebec et al. |
| 2013/0296792 A1 | 11/2013 | Cabiri |
| 2013/0296823 A1 | 11/2013 | Melker et al. |
| 2013/0298080 A1 | 11/2013 | Griffin et al. |
| 2013/0317753 A1 | 11/2013 | Kamen et al. |
| 2013/0324941 A1 | 12/2013 | Mann et al. |
| 2013/0331659 A1 | 12/2013 | Koski et al. |
| 2013/0332874 A1 | 12/2013 | Rosinko et al. |
| 2013/0338453 A1 | 12/2013 | Duke et al. |
| 2013/0338576 A1 | 12/2013 | O'Connor et al. |
| 2013/0346858 A1 | 12/2013 | Neyrinck |
| 2014/0005633 A1 | 1/2014 | Finan |
| 2014/0018730 A1 | 1/2014 | Stephan |
| 2014/0025400 A1 | 1/2014 | Galley et al. |
| 2014/0032549 A1 | 1/2014 | Mcdaniel et al. |
| 2014/0039383 A1 | 2/2014 | Dobbles et al. |
| 2014/0058749 A1 | 2/2014 | Galley et al. |
| 2014/0066859 A1 | 3/2014 | Ogawa et al. |
| 2014/0066886 A1 | 3/2014 | Roy et al. |
| 2014/0068487 A1 | 3/2014 | Steiger et al. |
| 2014/0073892 A1 | 3/2014 | Randloev et al. |
| 2014/0074033 A1 | 3/2014 | Sonderegger et al. |
| 2014/0088428 A1 | 3/2014 | Yang et al. |
| 2014/0091940 A1 | 4/2014 | Johnson et al. |
| 2014/0091941 A1 | 4/2014 | Johnson et al. |
| 2014/0094673 A1 | 4/2014 | Johnson et al. |
| 2014/0108046 A1 | 4/2014 | Echeverria et al. |
| 2014/0121635 A1 | 5/2014 | Hayter |
| 2014/0128705 A1 | 5/2014 | Mazlish |
| 2014/0128839 A1 | 5/2014 | Diianni et al. |
| 2014/0129951 A1 | 5/2014 | Amin et al. |
| 2014/0135880 A1 | 5/2014 | Baumgartner et al. |
| 2014/0142508 A1 | 5/2014 | Diianni et al. |
| 2014/0146202 A1 | 5/2014 | Boss et al. |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0317546 A1 | 10/2014 | Jacobson et al. |
| 2014/0325065 A1 | 10/2014 | Birtwhistle et al. |
| 2014/0344280 A1 | 11/2014 | Wei et al. |
| 2014/0358082 A1 | 12/2014 | Ohzawa |
| 2014/0380215 A1 | 12/2014 | Johnnie |
| 2014/0380218 A1 | 12/2014 | Johnnie |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0025498 A1 | 1/2015 | Estes |
| 2015/0025503 A1 | 1/2015 | Searle et al. |
| 2015/0041498 A1 | 2/2015 | Kakiuchi et al. |
| 2015/0073337 A1 | 3/2015 | Saint et al. |
| 2015/0080842 A1 | 3/2015 | Mathys |
| 2015/0112264 A1 | 4/2015 | Kamen et al. |
| 2015/0120317 A1 | 4/2015 | Mayou et al. |
| 2015/0134265 A1 | 5/2015 | Kohlbrecher et al. |
| 2015/0134353 A1 | 5/2015 | Ferrell et al. |
| 2015/0141912 A1 | 5/2015 | Estes |
| 2015/0165119 A1 | 6/2015 | Palerm et al. |
| 2015/0173674 A1 | 6/2015 | Hayes et al. |
| 2015/0193585 A1 | 7/2015 | Sunna |
| 2015/0202386 A1 | 7/2015 | Brady et al. |
| 2015/0205509 A1 | 7/2015 | Scriven et al. |
| 2015/0205511 A1 | 7/2015 | Vinna et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0227710 A1 | 8/2015 | Pappada |
| 2015/0253334 A1 | 9/2015 | Johnson et al. |
| 2015/0265767 A1 | 9/2015 | Vazquez et al. |
| 2015/0277722 A1 | 10/2015 | Masterson et al. |
| 2015/0289819 A1 | 10/2015 | Kamath et al. |
| 2015/0301691 A1 | 10/2015 | Qin |
| 2015/0306314 A1 | 10/2015 | Doyle et al. |
| 2015/0331995 A1 | 11/2015 | Zhao et al. |
| 2015/0351671 A1 | 12/2015 | Vanslyke et al. |
| 2015/0351672 A1 | 12/2015 | Vanslyke et al. |
| 2015/0356250 A1 | 12/2015 | Polimeni |
| 2016/0000998 A1 | 1/2016 | Estes |
| 2016/0015891 A1 | 1/2016 | Papiorek |
| 2016/0019352 A1 | 1/2016 | Cohen et al. |
| 2016/0038673 A1 | 2/2016 | Morales |
| 2016/0038675 A1 | 2/2016 | Estes et al. |
| 2016/0038689 A1 | 2/2016 | Lee et al. |
| 2016/0047771 A1* | 2/2016 | Mears .............. G01N 33/48785 |
| | | 204/406 |
| 2016/0051749 A1 | 2/2016 | Istoc |
| 2016/0058939 A1 | 3/2016 | Brewer et al. |
| 2016/0072841 A1 | 3/2016 | Caporal et al. |
| 2016/0082187 A1 | 3/2016 | Schaible et al. |
| 2016/0089491 A1 | 3/2016 | Smith |
| 2016/0089494 A1 | 3/2016 | Guerrini |
| 2016/0100807 A1 | 4/2016 | Johnson et al. |
| 2016/0103604 A1 | 4/2016 | Johnson et al. |
| 2016/0175520 A1 | 6/2016 | Palerm et al. |
| 2016/0193411 A1 | 7/2016 | Ljuhs et al. |
| 2016/0220181 A1 | 8/2016 | Rigoard et al. |
| 2016/0228641 A1 | 8/2016 | Gescheit et al. |
| 2016/0235913 A1 | 8/2016 | Smith et al. |
| 2016/0243318 A1 | 8/2016 | Despa et al. |
| 2016/0250422 A1 | 9/2016 | Koch et al. |
| 2016/0256087 A1 | 9/2016 | Doyle et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2016/0361494 A1 | 12/2016 | Jürg et al. |
| 2017/0003848 A1 | 1/2017 | Wakayanagi et al. |
| 2017/0007882 A1 | 1/2017 | Werner |
| 2017/0021096 A1 | 1/2017 | Cole et al. |
| 2017/0042487 A1 | 2/2017 | Johnson et al. |
| 2017/0049386 A1 | 2/2017 | Abraham et al. |
| 2017/0049957 A1 | 2/2017 | Michaud |
| 2017/0100538 A1 | 4/2017 | Mhatre et al. |
| 2017/0128021 A1 | 5/2017 | Kamath et al. |
| 2017/0128023 A1 | 5/2017 | Riback et al. |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0173261 A1 | 6/2017 | O'Connor et al. |
| 2017/0181629 A1 | 6/2017 | Mahalingam et al. |
| 2017/0181630 A1 | 6/2017 | Mahalingam et al. |

(56)                    References Cited

U.S. PATENT DOCUMENTS

| | | |
|---|---|---|
| 2017/0181645 A1 | 6/2017 | Mahalingam et al. |
| 2017/0188943 A1 | 7/2017 | Braig et al. |
| 2017/0189614 A1 | 7/2017 | Mazlish et al. |
| 2017/0189625 A1 | 7/2017 | Cirillo et al. |
| 2017/0199985 A1 | 7/2017 | Mazlish et al. |
| 2017/0203030 A1 | 7/2017 | Brewer et al. |
| 2017/0203036 A1 | 7/2017 | Mazlish et al. |
| 2017/0203037 A1 | 7/2017 | Desborough et al. |
| 2017/0203038 A1 | 7/2017 | Desborough et al. |
| 2017/0203039 A1 | 7/2017 | Desborough et al. |
| 2017/0216524 A1 | 8/2017 | Haider et al. |
| 2017/0224910 A1 | 8/2017 | Yodfat et al. |
| 2017/0232195 A1 | 8/2017 | Desborough et al. |
| 2017/0239415 A1 | 8/2017 | Hwang et al. |
| 2017/0242975 A1 | 8/2017 | Kahlbaugh |
| 2017/0258987 A1 | 9/2017 | Caspers |
| 2017/0281877 A1* | 10/2017 | Marlin et al. |
| 2017/0296746 A1 | 10/2017 | Chen et al. |
| 2017/0311903 A1 | 11/2017 | Davis et al. |
| 2017/0316592 A1 | 11/2017 | Kamath et al. |
| 2017/0332952 A1 | 11/2017 | Desborough et al. |
| 2017/0347971 A1 | 12/2017 | Davis et al. |
| 2017/0348482 A1 | 12/2017 | Duke et al. |
| 2018/0001006 A1 | 1/2018 | Schade et al. |
| 2018/0036495 A1 | 2/2018 | Searle et al. |
| 2018/0040255 A1 | 2/2018 | Freeman et al. |
| 2018/0042558 A1 | 2/2018 | Cabrera et al. |
| 2018/0042559 A1 | 2/2018 | Cabrera et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0085532 A1 | 3/2018 | Desborough et al. |
| 2018/0092576 A1 | 4/2018 | Afonso |
| 2018/0116589 A1* | 5/2018 | Mazlish ............... A61B 5/7275 |
| 2018/0126073 A1 | 5/2018 | Wu et al. |
| 2018/0133397 A1 | 5/2018 | Estes |
| 2018/0150614 A1 | 5/2018 | Sokolovskyy et al. |
| 2018/0161499 A1 | 6/2018 | Al-Ali et al. |
| 2018/0169334 A1 | 6/2018 | Grosman et al. |
| 2018/0200434 A1 | 7/2018 | Mazlish et al. |
| 2018/0200435 A1 | 7/2018 | Mazlish et al. |
| 2018/0200436 A1 | 7/2018 | Mazlish et al. |
| 2018/0200437 A1 | 7/2018 | Mazlish et al. |
| 2018/0200438 A1 | 7/2018 | Mazlish et al. |
| 2018/0200439 A1 | 7/2018 | Mazlish et al. |
| 2018/0200441 A1 | 7/2018 | Desborough et al. |
| 2018/0204636 A1 | 7/2018 | Edwards et al. |
| 2018/0207380 A1 | 7/2018 | Lantz et al. |
| 2018/0217917 A1* | 8/2018 | Hayter ................... G16H 10/40 |
| 2018/0277253 A1 | 9/2018 | Gondhalekar et al. |
| 2018/0279959 A1 | 10/2018 | Kamath et al. |
| 2018/0289333 A1 | 10/2018 | Kamath et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0369479 A1 | 12/2018 | Hayter et al. |
| 2019/0015025 A1* | 1/2019 | Desborough .......... G16H 20/13 |
| 2019/0076600 A1 | 3/2019 | Grosman et al. |
| 2019/0095052 A1 | 3/2019 | De et al. |
| 2019/0132801 A1 | 5/2019 | Kamath et al. |
| 2019/0184091 A1 | 6/2019 | Sjolund et al. |
| 2019/0240403 A1 | 8/2019 | Palerm et al. |
| 2019/0290844 A1 | 9/2019 | Monirabbasi et al. |
| 2019/0321545 A1 | 10/2019 | Saint |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2019/0374714 A1 | 12/2019 | Rioux et al. |
| 2020/0001006 A1 | 1/2020 | Pizzochero et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0113515 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |
| 2022/0105270 A1 | 4/2022 | Doyle et al. |

FOREIGN PATENT DOCUMENTS

| | | | |
|---|---|---|---|
| CA | 3026851 A1 | 2/2020 | |
| CN | 1297140 A | 5/2001 | |
| DE | 4200595 A1 | 7/1993 | |
| DE | 19627619 | 1/1998 | |
| DE | 19756872 A1 | 7/1999 | |
| DE | 10236669 A1 | 2/2004 | |
| EM | 0006276170001 | 1/2007 | |
| EM | 0006276170002 | 1/2007 | |
| EM | 0006276170003 | 1/2007 | |
| EM | 0007326490001 | 6/2007 | |
| EM | 0007326490002 | 6/2007 | |
| EM | 0031267050001 | 7/2016 | |
| EM | 0031267050002 | 7/2016 | |
| EM | 0031267050003 | 7/2016 | |
| EM | 0031267050004 | 7/2016 | |
| EP | 0062974 A1 | 10/1982 | |
| EP | 0275213 A2 | 7/1988 | |
| EP | 0496141 A1 | 7/1992 | |
| EP | 0549341 A1 | 6/1993 | |
| EP | 0580723 A1 | 2/1994 | |
| EP | 0612004 A1 | 8/1994 | |
| EP | 0721358 A1 | 7/1996 | |
| EP | 1045146 A2 | 10/2000 | |
| EP | 1136698 A1 | 9/2001 | |
| EP | 1177802 A1 | 2/2002 | |
| EP | 1495775 A1 | 1/2005 | |
| EP | 1527792 A1 | 5/2005 | |
| EP | 1571582 A2 | 9/2005 | |
| EP | 1754498 A1 | 2/2007 | |
| EP | 1818664 A1 | 8/2007 | |
| EP | 2397181 A1 | 12/2011 | |
| EP | 2468338 A1 | 6/2012 | |
| EP | 2500049 A1 | 9/2012 | |
| FR | 2096275 A5 | 2/1972 | |
| FR | 2585252 A1 | 1/1987 | |
| GB | 0747701 | 4/1956 | |
| GB | 2218831 A | 11/1989 | |
| JP | 51-125993 A | 11/1976 | |
| JP | 02-131777 A | 5/1990 | |
| JP | 2004-283378 A | 10/2004 | |
| JP | 2005-326943 A | 11/2005 | |
| JP | 2014-145594 A | 8/2014 | |
| JP | 2014145594 * | 8/2014 | ......... A61B 5/14532 |
| JP | 2018-153569 A | 10/2018 | |
| TW | M452390 U | 5/2013 | |
| WO | 86/06796 A1 | 11/1986 | |
| WO | 90/15928 A1 | 12/1990 | |
| WO | 95/09021 A1 | 4/1995 | |
| WO | 97/21457 A1 | 6/1997 | |
| WO | 98/00193 A1 | 1/1998 | |
| WO | 98/04301 A1 | 2/1998 | |
| WO | 98/11927 A1 | 3/1998 | |
| WO | 98/55073 A1 | 12/1998 | |
| WO | 98/57683 A1 | 12/1998 | |
| WO | 99/10040 A1 | 3/1999 | |
| WO | 99/10049 A1 | 3/1999 | |
| WO | 99/21596 A1 | 5/1999 | |
| WO | 99/39118 A1 | 8/1999 | |
| WO | 99/48546 A1 | 9/1999 | |
| WO | 99/56803 A1 | 11/1999 | |
| WO | 99/62576 A1 | 12/1999 | |
| WO | 00/30705 A1 | 6/2000 | |
| WO | 00/32258 A1 | 6/2000 | |
| WO | 00/48112 A2 | 8/2000 | |
| WO | 01/72354 A2 | 10/2001 | |
| WO | 01/72360 A1 | 10/2001 | |
| WO | 01/78812 A1 | 10/2001 | |
| WO | 01/91822 A1 | 12/2001 | |
| WO | 01/91833 A1 | 12/2001 | |
| WO | 02/15954 A1 | 2/2002 | |

(56)                    References Cited

FOREIGN PATENT DOCUMENTS

| | | | |
|---|---|---|---|
| WO | 02/26282 | A2 | 4/2002 |
| WO | 02/40083 | A2 | 5/2002 |
| WO | 02/43866 | A2 | 6/2002 |
| WO | 02/57627 | A1 | 7/2002 |
| WO | 02/68015 | A2 | 9/2002 |
| WO | 02/84336 | A2 | 10/2002 |
| WO | 2002/100469 | A2 | 12/2002 |
| WO | 03/16882 | A1 | 2/2003 |
| WO | 03/26726 | A1 | 4/2003 |
| WO | 03/97133 | A1 | 11/2003 |
| WO | 2003/103763 | A1 | 12/2003 |
| WO | 2004/043250 | A1 | 5/2004 |
| WO | 2004/056412 | A2 | 7/2004 |
| WO | 2004/092715 | A1 | 10/2004 |
| WO | 2004/110526 | A1 | 12/2004 |
| WO | 2005/002652 | A2 | 1/2005 |
| WO | 2005/039673 | A2 | 5/2005 |
| WO | 2005/051170 | A2 | 6/2005 |
| WO | 2005/072794 | A2 | 8/2005 |
| WO | 2005/072795 | A2 | 8/2005 |
| WO | 2005/082436 | A1 | 9/2005 |
| WO | 2005/110601 | A1 | 11/2005 |
| WO | 2005/113036 | A1 | 12/2005 |
| WO | 2006/053007 | A2 | 5/2006 |
| WO | 2006/067217 | A2 | 6/2006 |
| WO | 2006/097453 | A1 | 9/2006 |
| WO | 2006/105792 | A1 | 10/2006 |
| WO | 2006/105793 | A1 | 10/2006 |
| WO | 2006/105794 | A1 | 10/2006 |
| WO | 2007/064835 | A2 | 6/2007 |
| WO | 2007/066152 | A2 | 6/2007 |
| WO | 2007/078937 | A2 | 7/2007 |
| WO | 2007/141786 | A1 | 12/2007 |
| WO | 2008/024810 | A2 | 2/2008 |
| WO | 2008/029403 | A1 | 3/2008 |
| WO | 2008/133702 | A1 | 11/2008 |
| WO | 2009/039203 | A2 | 3/2009 |
| WO | 2009/045462 | A1 | 4/2009 |
| WO | 2009/049252 | A1 | 4/2009 |
| WO | 2009/066287 | A2 | 5/2009 |
| WO | 2009/066288 | A1 | 5/2009 |
| WO | 2009/098648 | A2 | 8/2009 |
| WO | 2009/134380 | A2 | 11/2009 |
| WO | 2010/022069 | A2 | 2/2010 |
| WO | 2010/053702 | A1 | 5/2010 |
| WO | 2010/077279 | A1 | 7/2010 |
| WO | 2010/132077 | A1 | 11/2010 |
| WO | 2010/138848 | A1 | 12/2010 |
| WO | 2010/139793 | A1 | 12/2010 |
| WO | 2010/147659 | A2 | 12/2010 |
| WO | 2011/031458 | A1 | 3/2011 |
| WO | 2011/075042 | A1 | 6/2011 |
| WO | 2011/095483 | A1 | 8/2011 |
| WO | 2011/133823 | A1 | 10/2011 |
| WO | 2011/163450 | A1 | 12/2011 |
| WO | 2012/045667 | A2 | 4/2012 |
| WO | 2012/073032 | A1 | 6/2012 |
| WO | 2012/108959 | A1 | 8/2012 |
| WO | 2012/134588 | A1 | 10/2012 |
| WO | 2012/177353 | A1 | 12/2012 |
| WO | 2012/178134 | A2 | 12/2012 |
| WO | 2013/050535 | A2 | 4/2013 |
| WO | 2013/078200 | A1 | 5/2013 |
| WO | 2013/134486 | A2 | 9/2013 |
| WO | 2013/149186 | A1 | 10/2013 |
| WO | 2013/177565 | A1 | 11/2013 |
| WO | 2013/182321 | A1 | 12/2013 |
| WO | 2014/029416 | A1 | 2/2014 |
| WO | 2014/035672 | A2 | 3/2014 |
| WO | 2014/109898 | A1 | 7/2014 |
| WO | 2014/110538 | A1 | 7/2014 |
| WO | 2014/149357 | A1 | 9/2014 |
| WO | 2014/179774 | A1 | 11/2014 |
| WO | 2014/194183 | A2 | 12/2014 |
| WO | 2015/056259 | A1 | 4/2015 |
| WO | 2015/061493 | A1 | 4/2015 |
| WO | 2015/073211 | A1 | 5/2015 |
| WO | 2015/081337 | A2 | 6/2015 |
| WO | 2015/117082 | A1 | 8/2015 |
| WO | 2015/117854 | A1 | 8/2015 |
| WO | 2015/167201 | A1 | 11/2015 |
| WO | 2015/177082 | A1 | 11/2015 |
| WO | 2015/187366 | A1 | 12/2015 |
| WO | 2016/004088 | A1 | 1/2016 |
| WO | 2016/022650 | A1 | 2/2016 |
| WO | 2016/041873 | A1 | 3/2016 |
| WO | 2016/089702 | A1 | 6/2016 |
| WO | 2016/141082 | A1 | 9/2016 |
| WO | 2016/161254 | A1 | 10/2016 |
| WO | 2017/004278 | A1 | 1/2017 |
| WO | 2017/091624 | A1 | 6/2017 |
| WO | 2017/105600 | A1 | 6/2017 |
| WO | 2017/184988 | A1 | 10/2017 |
| WO | 2017/187177 | A1 | 11/2017 |
| WO | 2017/205816 | A1 | 11/2017 |
| WO | 2018/009614 | A1 | 1/2018 |
| WO | 2018/067748 | A1 | 4/2018 |
| WO | 2018/111928 | A1 | 6/2018 |
| WO | 2018/120104 | A1 | 7/2018 |
| WO | 2018/136799 | A1 | 7/2018 |
| WO | 2018/204568 | A1 | 11/2018 |
| WO | 2019/077482 | A1 | 4/2019 |
| WO | 2019/094440 | A1 | 5/2019 |
| WO | 2019/213493 | A1 | 11/2019 |
| WO | 2019/246381 | A1 | 12/2019 |
| WO | 2020/081393 | A1 | 4/2020 |
| WO | 2021/011738 | A1 | 1/2021 |

OTHER PUBLICATIONS

Rodbard, David, "A Semilogarithmic Scale for Glucose Provides a Balanced View of Hyperglycemia and Hypoglycemia." J Diabetes Sci Technol. Nov. 1, 2009;3(6):1395-401. (Year: 2009).*

Xilas Temp Touch, "The latest in high-tech and convenient devices," DOCNews, vol. 2, No. 7, Jul. 1, 2005, http://docnews.diabetesjournals.ordlcgi/contenl/foll/2/7i 13, 3 pages.

Written Opinion of the International Searching Authority for PCT Application No. PCT/US2018/042082, mailed Sep. 7, 2018, six pages.

The Medtronic Diabetes Connection, 2006, 6 pages.

T:slimx2 Insulin Pump User Guide, Tandem Diabetes Care, Jul. 22, 2016.

Sara Krugman, Bionic Pancreas User Interface (3/4): Interface Details, Tidepool.org, Jul. 20, 2015.

Samuel Vozeh and Jean-Louis Steimer, Feedback Control Methods for Drug Dosage Optimisation, Concepts, Classification and Clinical Application, Clinical Pharmacokinetics, 10(6), pp. 457-476, Nov.-Dec. 1985.

Patent Abstracts of Japan, vol. 1999, No. 04, and JP 11 010036, Apr. 30, 1999 and Jan. 19, 1999, Toray Ind. Inc.

OmniPod Quick Start Guide, 2007, 2 pages.

OmniPod Insulin Management System—Investor Relations—Press Release, Feb. 1, 2005, http://investors.insulet.com/phoenix.zhtml?c=209336&p=irol-newsArticle&ID=988708&highlight= 1 page.

Michele Schiavon, Chiara Dalla Man, Yogish C. Kudva, Ananda Basu, and Claudio Cobelli, Quantitative Estimation of Insulin Sensitivity in Type 1 Diabetic Subjects Wearing a Sensor-Augmented Insulin Pump, Diabetes Care, vol. 37, pp. 1216-1223, May 2014.

Medtronic News Release, "Medtronic Receives FDA Approval for World's First Insulin Pump with Real-time Continuous Glucose Monitoring," Apr. 13, 2006, 3 pages.

JDRF, Statistics: JDRF and Diabetes, http://jdrf.org/about-jdrf/fact-sheets/jdrf-anddiabetes-statistics/, 2014.

International Search Report for PCT Application No. PCT/US2018/042082 mailed Sep. 7, 2018, 4 pages.

Hurley, Dan. Artificial Pancreas Makers Race to Market. Discover. Date published: Apr. 12, 2016. <http://discovermagazine.com/2016/may/13-priming-the-pump>.

(56)  References Cited

OTHER PUBLICATIONS

Guy A. Dumont, Feedback Control for Clinicians, Springer Science+ Media, Apr. 12, 2013, New York.
Fischer et al., In Vivo Comparison of Different Algorithms for the Artificial Beta-Cell, Artificial Organs, 9(2), International Society for Artificial Organs, May 1985, New York.
E. Salzsieder, G. Albrecht, E. Jutzi, and U. Fischer, Estimation of Individually Adapted Control Parameters for an Artificial Beta Cell, Biomedica Biochimica Acta. 43(5) pp. 585-596, May 1984.
Debiotech News Release, "Debiotech reveals its new miniaturized Disposable Insulin Nanopump™ for Diabetes therapy," available at http://www.debiotech.com/news/nw 159.html Apr. 24, 2006, 3 pages.
David A. Copp, Ravi Gondhalekar, and Joao P. Hespanha, Simultaneous Model Predictive Control and Moving Horizon Estimation for Blood Glucose Regulation in Type 1 Diabetes, Optimal Control Applications and Methods, Wiley InterScience, DOI: 10.1002/oca, pp. 1-15, Oct. 2016.
Dassau and Associates, 12-Week 24/7 Ambulatory Artificial Pancreas With Weekly Adaptation of Insulin Delivery Settings: Effect on Hemoglobin A1C and Hypoglycemia, Diabetes Care, Oct. 13, 2017.
Collins and Lee, "Microfluidic flow transducer based on the measurement of electrical admittance," Lab Chip, 2004, 4:7-10.
Centers for Disease Control and Prevention, Number (in Millions) of Adults with Diabetes by Diabetes Medication Status, United States, 1997-2011, http://www.cdc.gov/diabetes/statistics/meduse/fig1.htm, 2013.

Bigfoot Biomedical Reveals its Automated Insulin Delivery System. diaTribe. Date published: Jan. 25, 2016 <https://diatribe.org/bigfoot-biomedical-reveals-its-automated-insulin-delivery-system>.
Bhalla, Raveesh, Understanding Material Design Part II, Sep. 28, 2014, Medium.com [online], [site visited Apr. 11, 2018], Available from Internet: https://medium.com/@raveeshbhalla/understanding-material-design-cf2d60a16de3 (Year: 2014).
Accu-Chek Spirit, "Pump Therapy Made for You," Roche, 2006, 6 pages.
"Omnipod Horizon: Automated Glucose Control" Jun. 2017, 2 pages.
European Communication pursuant to Article 94(3) EPC for European Application No. 18749260.8, dated Feb. 23, 2021, 5 pages.
European Communication pursuant to Article 94(3) EPC for European Application No. 18749260.8, dated Apr. 5, 2023, 5 pages.
European Communication pursuant to Article 94(3) EPC for European Application No. 18755331.8, dated Aug. 11, 2023, 6 pages.
Notification of Oral Proceeding for European Application No. 18749260.8, dated Jan. 27, 2025, 8 pages.
Brief Communication of the Examining Division of European Patent Application No. 18749260.8, mailed May 9, 2025, 5 pages.
European Summons to attend oral proceedings pursuant to Rule 115(1) EPC for European Application No. 18755331.8, dated Jun. 18, 2025, 6 pages.

* cited by examiner

MULTI-SCALE DISPLAY OF BLOOD GLUCOSE INFORMATION

CROSS-REFERENCE TO RELATED APPLICATION

This application claims the benefit under 35 U.S.C. § 119(e) of U.S. Provisional Patent Application Ser. No. 62/532,167, filed Jul. 13, 2017, the disclosure of which is hereby incorporated herein in its entirety by this reference.

TECHNICAL FIELD

This document relates to a multi-scale display of blood glucose information and, more particularly, to the use of such a display in providing information regarding blood glucose levels of a person with diabetes (PWD).

BACKGROUND

People with Type I, Type II, or gestational diabetes must track their blood glucose levels and sometimes treat their condition to maintain appropriate blood glucose levels. Control of diabetes can include the monitoring of blood glucose levels using a blood glucose monitor (BGM) and sometimes a continuous glucose monitor (CGM). People with Type I, and some people with Type II or gestational diabetes, require insulin or an analog thereof. Because it cannot be taken orally, insulin is injected with a syringe or delivered subcutaneously by an external infusion pump. Excessive insulin delivery, however, can result in acute hypoglycemia, which can result in severe bodily injury and/or death. The failure to administer an appropriate amount of insulin to a person with diabetes, however, results in hyperglycemia, which can also result in severe bodily injury and/or death. Between the two conditions of hypoglycemia and hyperglycemia, hypoglycemia is more dangerous. Furthermore, dangerous levels of hypoglycemia are closer to normal levels than dangerous levels of hyperglycemia. Because of the risks involved, there is a need for an improved system for providing information regarding blood glucose levels.

The subject matter claimed in the present disclosure is not limited to embodiments that solve any disadvantages or that operate only in environments such as those described above. Rather, this background is only provided to illustrate one example of a technology area where some embodiments described in the present disclosure may be practiced.

BRIEF SUMMARY

Medication delivery systems, methods, and devices provided herein include at least a blood glucose monitor and/or monitoring device (e.g., a BGM, a CGM, etc.) and a display device (e.g., a smartphone, tablet, personal computer, or wearable device having an installed app, an installed browser executing a browser application, an installed browser or app receiving information from a server, etc.). In some cases, the display device can serve as the primary user interface for providing blood glucose level information to a user. In some cases, the methods, devices, and systems provided herein can include an insulin delivery device (e.g., an insulin pump, a smart insulin pen, a connected dose-capture cap for an insulin pen, etc.) in communication with or part of the blood glucose monitoring device and/or the display device. In some cases, the display device may be configured to monitor or otherwise obtain blood glucose levels and display those levels to a user of the device. For example, the display device may present the current blood glucose level on the display device based on a first scale, such as a logarithmic scale. The display device may display historical glucose levels on a second scale, such as a linear scale. In these and other embodiments, the second scale may be based on or anchored to the first scale. For example, the current blood glucose level may be displayed at a location based on a logarithmic scale along the vertical axis of the display, and the historical blood glucose levels may be displayed as a continuous line starting at the current blood glucose level using a linear scale. Thus, the display device may display the current blood glucose level according to a first scale and the historical blood glucose levels according to a second scale.

In some cases, the display device can project a future blood glucose level. The projected future blood glucose levels can also be displayed according to the second scale and anchored to the current blood glucose level presented based on the first scale. For example, the historic, current, and projected future blood glucose levels may all be displayed on a continuous line according to a linear scale. The location of the line along the vertical axis of the display device may be anchored to the location of the current blood glucose level based on a logarithmic scale.

One or more embodiments of the present disclosure may include a system for displaying blood glucose information that includes a blood glucose monitoring device configured to monitor blood glucose levels of a user, and a display. The system may also include one or more processors, and a non-transitory computer-readable medium containing instructions that, when executed by the one or more processors, cause the system to perform operations. The operations may include obtaining the blood glucose levels from the blood glucose monitoring device, where the blood glucose levels include at least a current blood glucose level and a historic blood glucose level. The operations may also include presenting the current blood glucose level at a first location on the display based on a first scale, and presenting the historic blood glucose level at a second location on the display based on a second scale different from the first scale.

One or more embodiments of the present disclosure may include a method of displaying blood glucose information. The method may include monitoring blood glucose levels of a user, where the blood glucose levels include at least a current blood glucose level and a historic blood glucose level. The method may also include presenting the current blood glucose level using a point indicator along an approximately horizontally centered axis based on a non-linear scale, and presenting the historic blood glucose level and a predicted future blood glucose level on the display as a single smoothed curve passing the point indicator.

The details of one or more implementations of various embodiments are set forth in the accompanying drawings and the description below. Other features, objects, and advantages of the various embodiments will be apparent from the description and drawings, and from the claims.

It is to be understood that both the foregoing general description and the following detailed description are merely examples and explanatory and are not restrictive of the claims.

BRIEF DESCRIPTION OF THE DRAWINGS

Example embodiments will be described and explained with additional specificity and detail through the use of the accompanying drawings in which.

DETAILED DESCRIPTION

Figure 1:
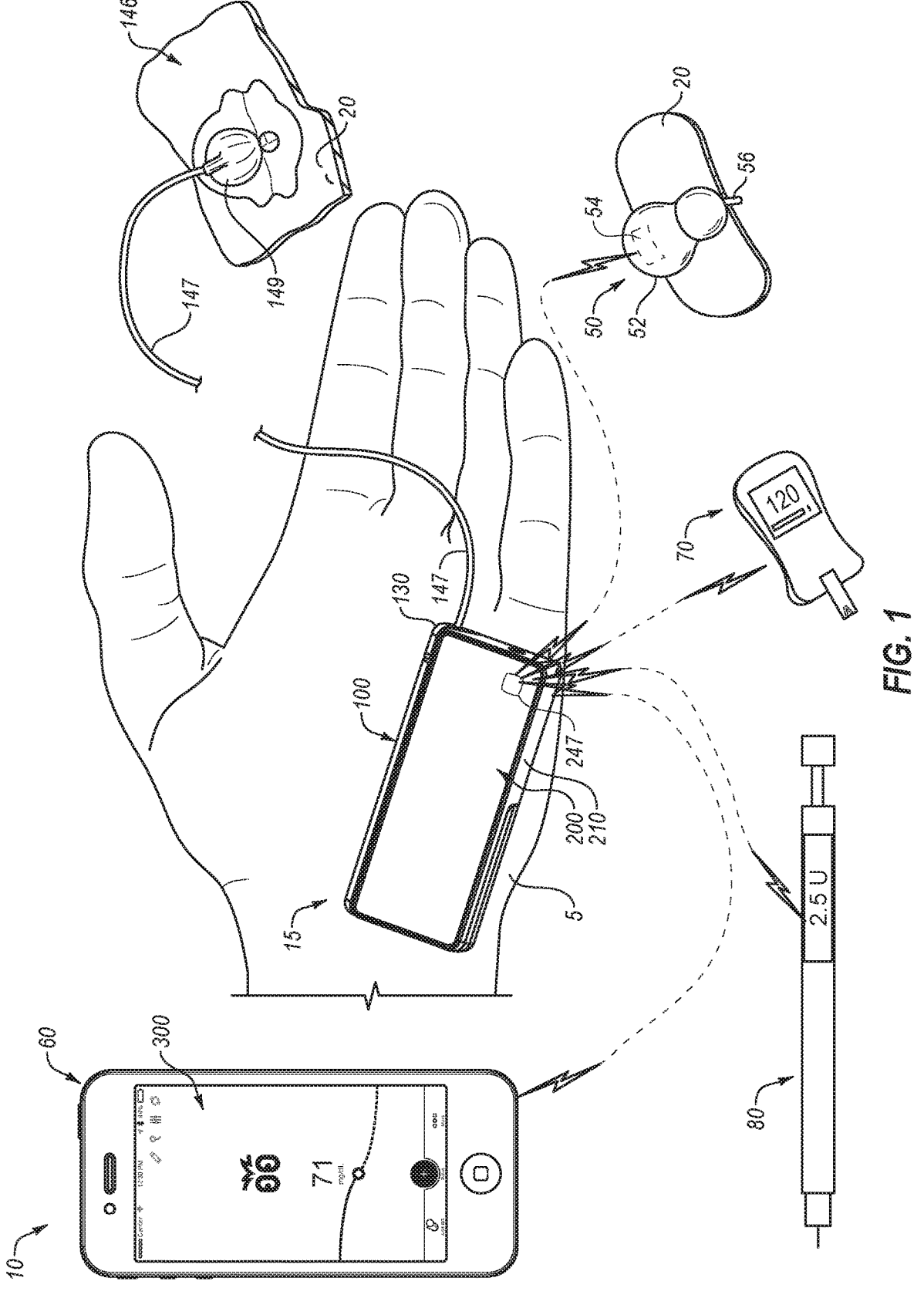
FIG. 1 provides an example system to display blood glucose information using multiple scales.

FIG. 1 provides an example system to display blood glucose information using multiple scales, in accordance with one or more embodiments of the present disclosure. The system of FIG. 1 may be described as a diabetes management system 10. The system 10 may include a pump assembly 15 for providing insulin and a continuous glucose monitor 50. As shown, the continuous glucose monitor 50 is in wireless communication with pump assembly 15. In some cases, a continuous glucose monitor can be in wired communication with pump assembly 15. In some cases, not shown, a continuous glucose monitor can be incorporated into an insulin pump assembly. As shown, pump assembly 15 can include a reusable pump controller 200 that forms part of the pump assembly 15. In some cases, reusable pump controller 200 is adapted to determine one or more basal delivery rates. In some cases, continuous glucose monitor 50 can act as a controller adapted to communicate basal delivery rates to pump assembly 15.

Pump assembly 15, as shown, can include reusable pump controller 200 and a disposable pump 100, which can contain a reservoir for retaining insulin. A drive system for pushing insulin out of the reservoir can be included in either the disposable pump 100 or the reusable pump controller 200 in a controller housing 210. Reusable pump controller 200 can include a wireless communication device 247, which can be adapted to communicate with a wireless communication device 54 of continuous glucose monitor 50 and other diabetes devices in the system, such as those discussed below. In some cases, pump assembly 15 can be sized to fit within a palm of a hand 5. Pump assembly 15 can include an infusion set 146. Infusion set 146 can include a flexible tube 147 that extends from the disposable pump 100 to a subcutaneous cannula 149 that may be retained by a skin adhesive patch (not shown) that secures the subcutaneous cannula 149 to the infusion site. The skin adhesive patch can retain the cannula 149 in fluid communication with the tissue or vasculature of the PWD so that the medicine dispensed through tube 147 passes through the cannula 149 and into the PWD's body. A cap device 130 can provide fluid communication between an output end of an insulin cartridge (not shown) and tube 147 of infusion set 146. Although pump assembly 15 is depicted as a two-part insulin pump, one piece insulin pumps are also contemplated. Additionally, insulin pump assemblies used in methods and systems provided herein can alternatively be a patch pump.

Continuous glucose monitor 50 (e.g., a glucose monitoring device) can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of the PWD's blood glucose level or the like. In some cases, the sensor shaft 56 can measure glucose or another analyte in interstitial fluid or in another fluid and correlate that to blood glucose levels. In response to the measurements made by the sensor shaft 56, the continuous glucose monitor 50 can employ the wireless communication device 54 to transmit data to a corresponding wireless communication device 247 housed in the pump assembly 15. In some cases, the continuous glucose monitor 50 may include a circuit that permits sensor signals (e.g., data from the sensor shaft 56) to be communicated to the wireless communication device 54. The wireless communication device 54 can transfer the collected data to reusable pump controller 200 (e.g., by wireless communication to the wireless communication device 247). Additionally or alternatively, the system 10 may include another glucose monitoring device that may utilize any of a variety of methods of obtaining information indicative of a PWD's blood glucose levels and transferring that information to reusable pump controller 200. For example, an alternative monitoring device may employ a micropore system in which a laser porator creates tiny holes in the uppermost layer of a PWD's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. In other examples, the monitoring device can include detect glucose levels using equilibrium fluorescence detectors (e.g., sensors including a diboronic acid receptor attached to a fluorophore). Furthermore, it should be understood that in some alternative implementations, continuous glucose monitor 50 can be in communication with reusable pump controller 200 or another computing device via a wired connection. In some cases, continuous glucose monitor 50 can be adapted to provide blood glucose measurements for a PWD when in use for the PWD at regular or irregular time intervals. In some cases, continuous glucose monitor 50 can detect blood glucose measurements at least every thirty minutes, at least every fifteen minutes, at least every ten minutes, at least every five minutes, or about every minute. In some cases, continuous glucose monitor 50 can itself determine a basal delivery rate using methods provided herein and communicate that basal rate to the pump assembly 15. In some cases, continuous glucose monitor 50 can transmit blood glucose measurement data to reusable pump controller 200 and reusable pump controller 200 can use methods provided herein to determine a basal delivery rate. In some cases, a remote controller can receive glucose data from continuous glucose monitor 50, determine a basal delivery rate using methods provided herein, and communicate the basal rate to pump assembly 15.

Diabetes management system 10 may optionally include a blood glucose meter 70 (e.g., a glucose sensor). In some cases, blood glucose meter 70 can be in wireless communication with reusable pump controller 200. Blood glucose meter 70 can take a blood glucose measurement using one or more test strips (e.g., blood test strips). A test strip can be inserted into a strip reader portion of the blood glucose meter 70 and then receive the PWD's blood to determine a blood glucose level for the PWD. In some cases, the blood glucose meter 70 is configured to analyze the characteristics of the PWD's blood and communicate (e.g., via a BLUETOOTH® wireless communication connection) the information to reusable pump controller 200. In some cases, a user can manually input a glucose meter reading. The blood glucose meter 70 can be manually operated by a user and may include an output subsystem (e.g., display, speaker) that can provide the user with blood glucose readings that can be subsequently entered into the reusable pump controller 200 or user interface to collect the data from an unconnected BGM into the system. The blood glucose meter 70 may be configured to communicate data (e.g., blood glucose readings) obtained to reusable pump controller 200 and/or other devices, such as a display device 60 (e.g., a control device). Such communication can be over a wired and/or wireless connection, and the data can be used by system 10 for a number of functions (e.g., calibrating the continuous glucose monitor 50, confirming a reading from the continuous glucose monitor 50, determining a more accurate blood glucose reading for a bolus calculation, detecting a blood glucose level when the continuous glucose monitor 50 is malfunctioning).

In some cases, the system 10 can further include a display device 60 that can communicate with the reusable pump controller 200 through a wireless and/or wired connection with the reusable pump controller 200 (e.g., via a BLUETOOTH® wireless communication connection or a near-field communication connection). In some cases, the display device 60 communicates wirelessly with other diabetes devices of system 10. The display device 60 can be any of a variety of appropriate computing devices, such as a smartphone, a tablet computing device, a wearable computing device, a smartwatch, a fitness tracker, a laptop computer, a desktop computer, and/or other appropriate computing devices. In some cases (for example, where the reusable pump controller 200 does not determine a basal delivery rate), the display device 60 can receive and log data from other elements of the system 10 and determine basal delivery rates using any method or approach, for example, selecting a basal delivery rate or a number of basal delivery rates that produce lowest cost function values, and any method or approach described in U.S. Patent Publication 2017/0332952, published Nov. 23, 2017 and entitled "INSULIN DELIVERY SYSTEM AND METHODS WITH RISK BASED SET POINTS" (hereinafter, "Desborough"), the entire contents and disclosure of which are hereby incorporated herein by this reference. In some cases, the basal delivery rate may be based at least in part on projected blood glucose levels. For example, the display device 60 may predict future blood glucose levels based on historical readings, current IOB, expected delivery rate, etc. The display device 60 may project and/or predict future blood glucose levels in any predictive manner, including the example set forth below and/or as set forth in Desborough.

Example Techniques for Predicting Future Blood Glucose Values

Systems and methods provided herein can use any suitable physiology model to predict future blood glucose values (represented as $BG_t$ and $\gamma_t$). In some cases, methods and systems provided herein can predict future blood glucose values using past and current carbohydrate, insulin, and blood glucose values.

Systems and methods provided herein can in some cases estimate a first future blood glucose using a model. In some cases, blood glucose can be approximated using two determinist Integrating first order plus dead time (FOPDT) models for the effect of carbohydrates and insulin, combined with an autoregressive (AR2) disturbance model. Accordingly, blood glucose (BG) at time (t) can be estimated using the following equation:

$$BG_t = \gamma_t = BGc_t + BGi_t + BGd_t = G_cC_t + G_i i_t + G_d e^{\alpha t}$$

From the equation above, the first element may represent the effect on blood glucose due to carbohydrates:

$$G_c = \frac{K_c(1-\alpha_c)B^{C_{dt}}}{(1-\alpha_c B)(1-B)}$$

where:
B is the backward shift operator such that $B\gamma_t = \gamma_{t-1}$, $B^2\gamma_t = \gamma_{t-2}$, $B^k\gamma_t = \gamma_{t-k}$ $$k_c = \frac{ISF}{CR}$$

is the carb gain (in units of mg/dl/g)

$$\alpha_c = e^{-\frac{ts}{\tau_c}},$$

where $\tau_c$ is the carb time constant (for example, approximately 30 minutes), and
where ts is the sampling time (for example, a CGM may use a sampling time interval of every 5 minutes),
$c_{dt}$=floor($\tau_{dc}$/ts), where $\tau_{dc}$ is the carb deadtime (for example, approximately 15 minutes)

From the equation above, the second element may represent the effect on blood glucose due to insulin:

$$G_i = \frac{K_i(1-\alpha_c)B^{i_{dt}}}{(1-\alpha_i B)(1-B)}$$

where:
$k_i$=−ISF is the insulin gain (in units of mg/dl/unit), $$\alpha_i = e^{-\frac{ts}{\tau_i}},$$

where $\tau_i$ is the insulin time constant (for example, approximately 120 minutes),
$i_{dt}$=floor($\tau_{di}$/ts), where $\tau_{di}$ is the insulin deadtime (for example, approximately 30 minutes), From the equation above, the third element may represent the effect on blood glucose due to disturbances (e.g., the AR2 disturbance model):

$$G_d e^{\alpha t}$$

and may be based on the following log-transformed AR2 model:

$$\ln\left(\frac{BGd_t}{\mu^*}\right) = \alpha_1 \ln\left(\frac{BGd_t}{\mu^*}\right) + \alpha_2 \ln\left(\frac{BGd_{t-2}}{\mu^*}\right) + \alpha_t$$

which when rearranged, yields:

$$BGd_t = BGd_{t-1}^{\alpha_1} BGd_{t-2}^{\alpha_2} \mu^{*(1-\alpha_1-\alpha_2)} e^{\alpha_t}$$

where, in some examples, $$\alpha_t \sim \text{Normal}(0, \sigma_\alpha)$$

and $$\sigma_a \approx 50\% \; \ln(\sigma^*) \sqrt{\frac{1+\alpha_2}{1-\alpha_2}((1-\alpha_2)^2) - \alpha_1^2}$$

with
$\mu^* \sim 10^{Normal(2.09, \; 0.08)}$ and $\sigma^* \sim 10^{Normal(0.15, \; 0.028)}$ such that
$\alpha_1 \approx 1.6442$, $\alpha_2 \approx 0.6493$.

Using the above notation, expansion of the initial equation for $BG_t$ may be represented by the equation:

$$BG_t = \frac{k_c(1-\alpha_c)}{(1-\alpha_c B)(1-B)} c_{t-dt_c} + \frac{k_i(1-\alpha_i)}{(1-\alpha_i B)(1-B)} i_{t-dt_i} + BGd_{t-1}^{\alpha_1} BGd_{t-2}^{\alpha_2} \mu^{*(1-\alpha_1-\alpha_2)}$$

Systems and methods provided herein can in some cases calculate an amount of insulin on board (IOB) and/or an amount of carbohydrates on board (COB) in order to predict future blood glucose values. IOB and COB represent the amount of insulin and carbohydrates, respectively, which have been infused and/or consumed but not yet metabolized. Knowledge of IOB and COB can be useful for a user of a method or system provided herein when it comes to bolus decisions to prevent insulin stacking, but knowledge of IOB and COB can also be used in methods and systems provided herein to predict future blood glucose values.

IOB and COB represent the amount of insulin and carbohydrates, respectively, which have been infused and/or consumed but not yet metabolized. Knowledge of IOB can be useful in correcting bolus decisions to prevent insulin stacking. Knowledge of IOB and COB can be useful for predicting and controlling blood glucose. Both insulin infusion and carbohydrate consumption can involve deadtime or transportation delay (e.g., it can take ten to forty minutes for insulin and/or carbohydrates to begin to affect blood glucose). During the period immediately after entering the body (e.g., during the deadtime period), it can be beneficial to account for IOB and COB in any decisions such as bolusing. This can be called "Decision" IOB/COB. "Action" IOB/COB, on the other hand, can represent the insulin and/or carbohydrates available for action on blood glucose. In some cases, Decision IOB can be a displayed JOB, while Action IOB can be an IOB determined for use in selecting a basal delivery rate or profile in methods and systems provided herein.

From the equations above, $$BG_{it} = \frac{-ISF(1-\alpha_i)B^{idt}}{(1-\alpha_i B)(1-B)} i_{t-i_{dt}}$$

where $$BY_t = Y_{t-1}, B^2 Y_t = Y_{t-2}, B^k Y_t = Y_{t-k}$$

$$\alpha_i = e^{-\frac{ts}{\tau_i}}$$

where $\tau_i$ is the insulin time constant (for example, approximately 120 minutes) $i_{dt} = \text{floor}(\tau_{dt}/ts)$, where $\tau_{di}$ is the insulin deadtime (for example, approximately 30 minutes) and where ts is the sampling time (for example, a CGM may use a sampling time interval of every 5 minutes)

"Decision" IOB

In some embodiments, Decision IOB at time (t) (IOB_D$_t$) may be calculated according to the following mathematical process:

$$IOB\_D_t = IOB\_D_{t-1} - \frac{BGi_t - BGi_{t-1}}{-ISF} + i_t$$

or, alternatively, $$\nabla IOB\_D_t = -\frac{\nabla BGi_t}{-ISF} + i_t$$

substituting the equation above for $BG_{it}$ into the equation for IOB D$_t$ or $\nabla IOB\_D_t$ yields $$IOB_{D_t} = \frac{1 - \alpha_i B - (1-\alpha_i)B^i dt}{1 - (\alpha_i + 1)B + \alpha_i B^2} i_t$$

or, alternatively, $$\nabla IOB\_D_t = -\frac{1-\alpha_i}{1-\alpha_i B} i_{t-i_{dt}} + i_t$$

"Action" IOB

In some embodiments, Action IOB at time (t) (IOB_A$_t$) may be calculated according to the following mathematical process:

$$IOB\_A_t = \frac{1}{1-\alpha_i B} i_{t-i_{dt}}$$

For an arbitrary series of insulin infusions, using an infinite series of expansions of $$\frac{1}{1-\alpha_i B}, IOB\_A_t$$

may be represented by $$IOB_{A_t} = \sum_{k=0}^{n} \alpha_i^k i_{t-k-i_{dt}}$$

Stated another way, $$BGi_t = \frac{-ISF(1-\alpha_i)}{1-B}IOB\_A_t$$

The formulas for COB, including Action COB and Decision COB, may be developed in a similar fashion, using the equation above related to $G_c$:

$$G_{ct} = \frac{k_c(1-\alpha_c)B^{c_{dt}}}{(1-\alpha_c B)(1-B)}$$

Accordingly, future blood glucose data can be estimated using current or recent blood glucose data, data about when carbohydrates were consumed, and/or data regarding when insulin was and/or will be administered. Moreover, because evaluated insulin delivery profiles and/or rates include basal insulin delivery rates above and below the BBR, those insulin delivery rates above BBR can be added to the IOB calculation and insulin delivery rates below the BBR can be subtracted from the IOB. In some cases, a variation in a Decision IOB due to actual variations from BBR can be limited to positive deviations in order to prevent a user from entering an excessive bolus.

In some cases, a user can input relevant data into the display device 60. In some cases, the display device 60 can be used to transfer data from the reusable pump controller 200 to another computing device (e.g., a back-end server or a cloud-based device). In some cases, the display device 60 provides a user interface (e.g., graphical user interface (GUI), speech-based user interface, motion-controlled user interface) through which users can provide information to control operation of the reusable pump controller 200 and the system 10. For example, the display device 60 can be a mobile computing device running a mobile app that communicates with reusable pump controller 200 over short-range wireless connections (e.g., BLUETOOTH® connection, Wi-Fi Direct connection, near-field communication connection, etc.) to provide status information for the system 10 and allow a user to control operation of the system 10 (e.g., toggle between delivery modes, adjust settings, log food intake, change a fear of hypoglycemia index (FHI), confirm/modify/cancel bolus dosages, and the like).

By way of further characterization, a GUI typically includes one or more information regions and active/activatable regions. As used in this disclosure, an information region is a region of a GUI which presents information to a user. An activatable region is a region of a GUI, such as a button, slider, or a menu, which allows the user to take some action with respect to the GUI (e.g., if manipulated, such as with a point-and-click interface, a touch interface, an audio interface, etc.). Some information regions are also activatable regions in that they present information and enable some action that may be taken by a user. Activatable regions may be displayed as GUI elements/objects, for example, buttons, sliders, selectable panes, menus, etc., all of various shapes and sizes.

Generally, if an interaction is detected by a GUI, a process is used to determine the activatable regions of the GUI to which the contact corresponds, if any. For example, if a touch is detected at an "ENTER," then responsive to the detected touch a process may determine that the contact was at the ENTER button. The ENTER button is an activatable region, so one or more events may be created at the GUI and/or an underlying application that invoked the GUI.

Optionally, system 10 may include a bolus administering device 80 (e.g., a syringe, an insulin pen, a smart syringe with device communication capabilities, or the like) through which bolus dosages can be manually administered to a PWD. In some cases, a suggested dosage for a bolus to be administered using the bolus administering device 80 can be output to a user via the user interface of reusable pump controller 200 and/or the user interface of the display device 60. In some cases, the bolus administering device 80 can communicate through a wired and/or wireless connection with reusable pump controller 200 and/or the display device 60. In some cases, system 10 can allow users to input insulin deliveries made using a syringe or insulin pen.

In some cases, the display device 60 includes a display 300. The display device 60 can display blood glucose information. For example, the display device 60 may obtain blood glucose readings from the CGM 50 or the blood glucose meter 70. The display device 60 may store the blood glucose readings as historic blood glucose readings and the most recent blood glucose level as the current blood glucose level. The display device 60 may display various aspects of the blood glucose levels and/or projected blood glucose levels as explained in greater detail below.

While one embodiment of a diabetes management system is illustrated in FIG. 1, it will be appreciated that any number, type, or style of diabetes management devices may be utilized in conjunction with the present disclosure. For example, a patch pump, a syringe, etc., may be utilized to enter doses of insulin delivered to a PWD. As another example, any blood glucose reading device may be utilized, such as a BGM, a CGM, a flash glucose monitor (FGM), or any other blood glucose reading device. In some embodiments, an insulin delivery device may not be used.

Modifications, additions, or omissions may be made to FIG. 1 without departing from the scope of the present disclosure. For example, the system 10 may include any type or style of insulin delivery devices and/or monitoring devices. As another example, the display device 60 may take any form or style of computing device. As an additional example, the display device 60 may be coupled with a remote cloud device (not illustrated) that may store one or more aspects of the monitored and/or projected blood glucose levels and/or insulin delivery rates and/or projections. Such a cloud device may be accessible by a third party (e.g., a physician) or a PWD.

Figure 2:
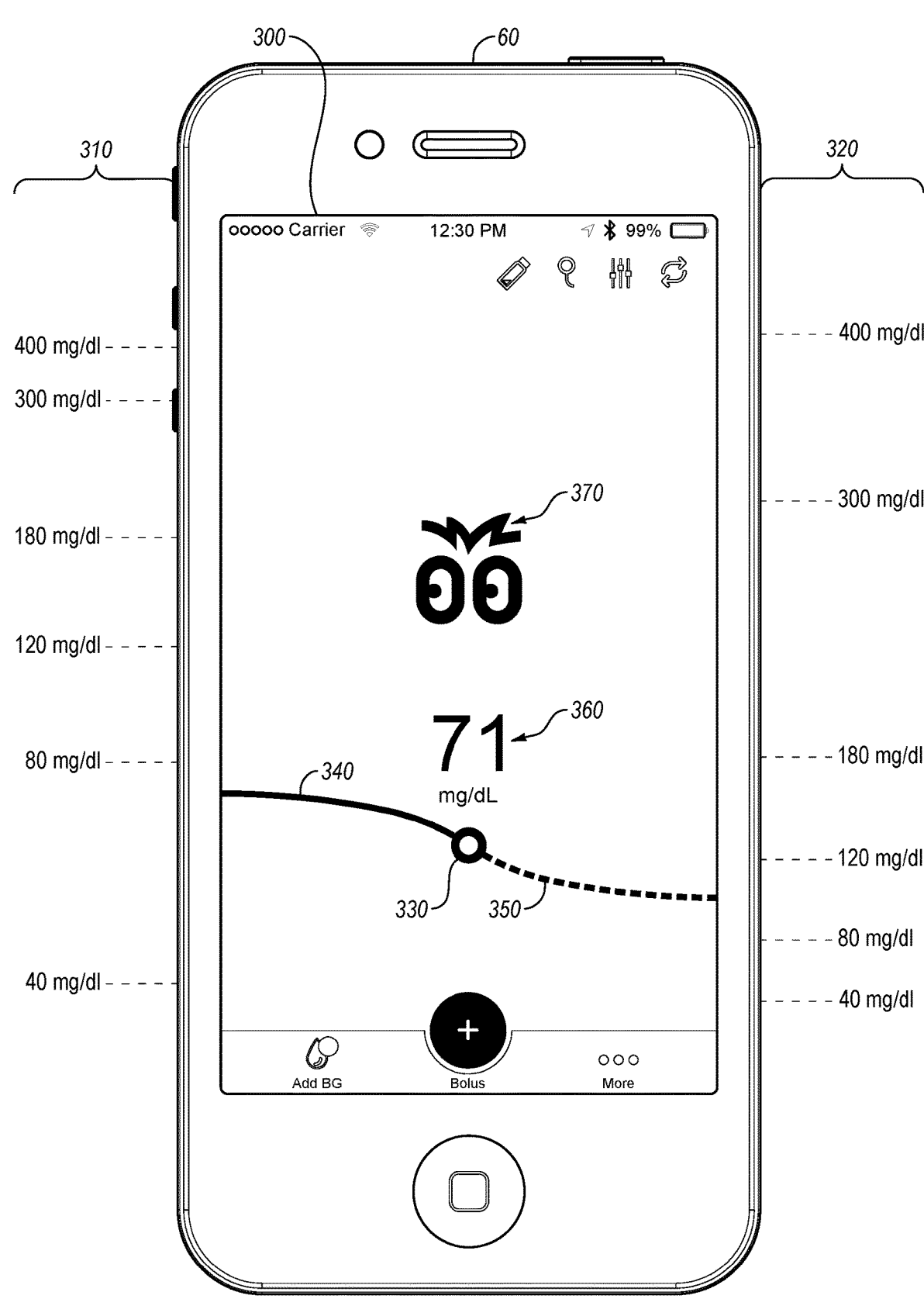
FIG. 2 is an example display of blood glucose information using multiple scales.

FIG. 2 is an example display 300 of blood glucose information using multiple scales, in accordance with one or more embodiments of the present disclosure. The display 300 may be part of the display device 60 of FIG. 1. The display 300 may present blood glucose information based on a first scale 310 and a second scale 320. In some cases, the display 300 may present a current blood glucose level 330, historic blood glucose levels 340, and projected blood glucose levels 350. Additionally or alternatively, the display 300 may include a numerical representation 360 of the current blood glucose level 330 and/or an avatar 370 for a glanceable view of blood glucose information.

In some embodiments, the blood glucose information may be displayed on the display 300 using both the first scale 310 and the second scale 320. As illustrated in FIG. 2, the first scale 310 may be a risk-based scale such that areas of greater risk may receive more of the total space of the display 300. For example, the risk of blood glucose levels of a PWD going below normal blood glucose levels (e.g., hypoglycemia) may be more severe than the risks of a PWD going above normal blood glucose levels (e.g., hyperglycemia).

Using a risk-based scale, blood glucose levels corresponding to hypoglycemia may cover a larger portion of the display 300 than other scales.

The first scale 310 may include a logarithmic scale such that lower values receive logarithmically more space of the display 300. For example, as illustrated in FIG. 2, according to the first scale 310, the range from 400 mg/dL to 180 mg/dL may cover approximately 35% of the display 300 used for blood glucose information, the range from 180 mg/dL to 80 mg/dL may cover approximately 35% of the display 300 used for blood glucose information, and the range from 80 mg/dL to 40 mg/dL may cover approximately 30% of the display 300 used for blood glucose information.

The second scale 320 may illustrate a linear scale that also covers the display 300 used for displaying blood glucose information. For example, as illustrated in FIG. 2, according to the second scale 320, the range from 400 mg/dL to 180 mg/dL covers approximately 61% of the display 300 used for blood glucose information, the range from 180 mg/dL to 80 mg/dL covers approximately 28% of the display 300 used for blood glucose information, and the range from 80 mg/dL to 40 mg/dL covers approximately 11% of the display 300 used for blood glucose information. In these and other embodiments, the second scale 320 may provide a framework within which various aspects of blood glucose information may be displayed. Intuitively, some users such as PWDs may more readily understand and relate to a linear scale (such as the second scale 320) as opposed to a logarithmic scale (such as the first scale 310).

In some embodiments, the current blood glucose level 330 may be displayed based on the first scale 310. For example, an icon, marker, or other indication of the current blood glucose level 330 may be displayed along a vertical axis of the display 300 based on the logarithmic first scale 310. In some embodiments, the current blood glucose level 330 may be displayed at approximately the center of the display 300 along a horizontal axis of the display 300. Additionally or alternatively, the current blood glucose level 330 may move along a vertical axis along the center of the horizontal axis as changes occur in the current blood glucose level 330.

In some cases, the current blood glucose level 330 may be based on a BGM, a CGM, an FGM, or any other blood glucose monitoring device. In these and other cases, "current" blood glucose levels may include the most recent blood glucose reading, a blood glucose reading within a time threshold (e.g., within the last 1 minute, within the last 2 minutes, within the last 5 minutes, within the last 10 minutes, within the last 15 minutes, etc.), or combinations thereof. In some embodiments, an icon representing the current blood glucose level 330 may change based on how recent the latest reading has been taken. For example, the color of the icon may fade over time, or the icon may no longer be present after a certain duration of time, etc.

In some embodiments, the historic blood glucose levels 340 and/or the projected blood glucose levels 350 may be displayed according to the second scale 320. In some embodiments, the second scale 320 may be anchored or oriented based on the first scale 310. Examples, of such anchoring may be explained in greater detail with reference to FIGS. 3 and/or 4. The second scale 320 may be displayed in FIG. 2 to illustrate variations in the amount of the display 300 covered by various spans of blood glucose levels according to the first scale 310 and the second scale 320.

By displaying blood glucose information using the first scale 310, a greater visual distinction is observable for hypoglycemic ranges as compared to the second scale 320.

Furthermore, using the first scale 310, the range of 300-400 mg/dL (which is rarely used) only uses approximately 10% of the display 300 rather than over 25% of the display 300 when using the second scale 320.

Figure 6A:
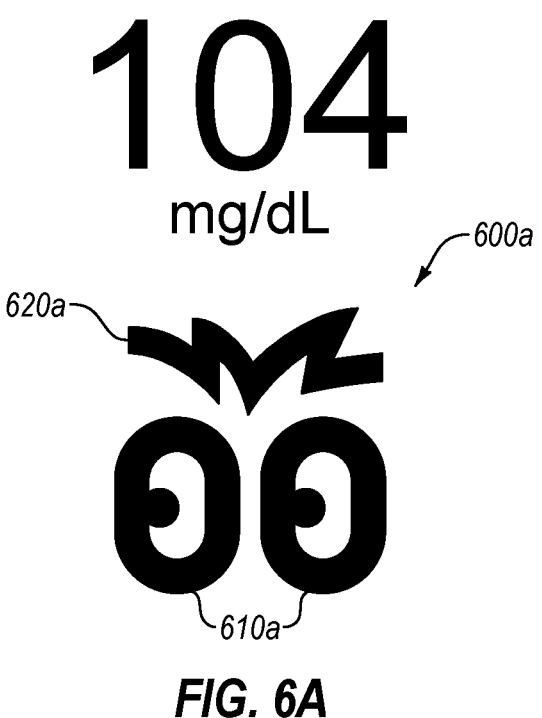
FIGS. 6A and 6B illustrate example features of a display of blood glucose information.

The avatar 370 for glanceability may be described with greater detail with reference to FIGS. 6A and/or 6B.

Figure 3A:
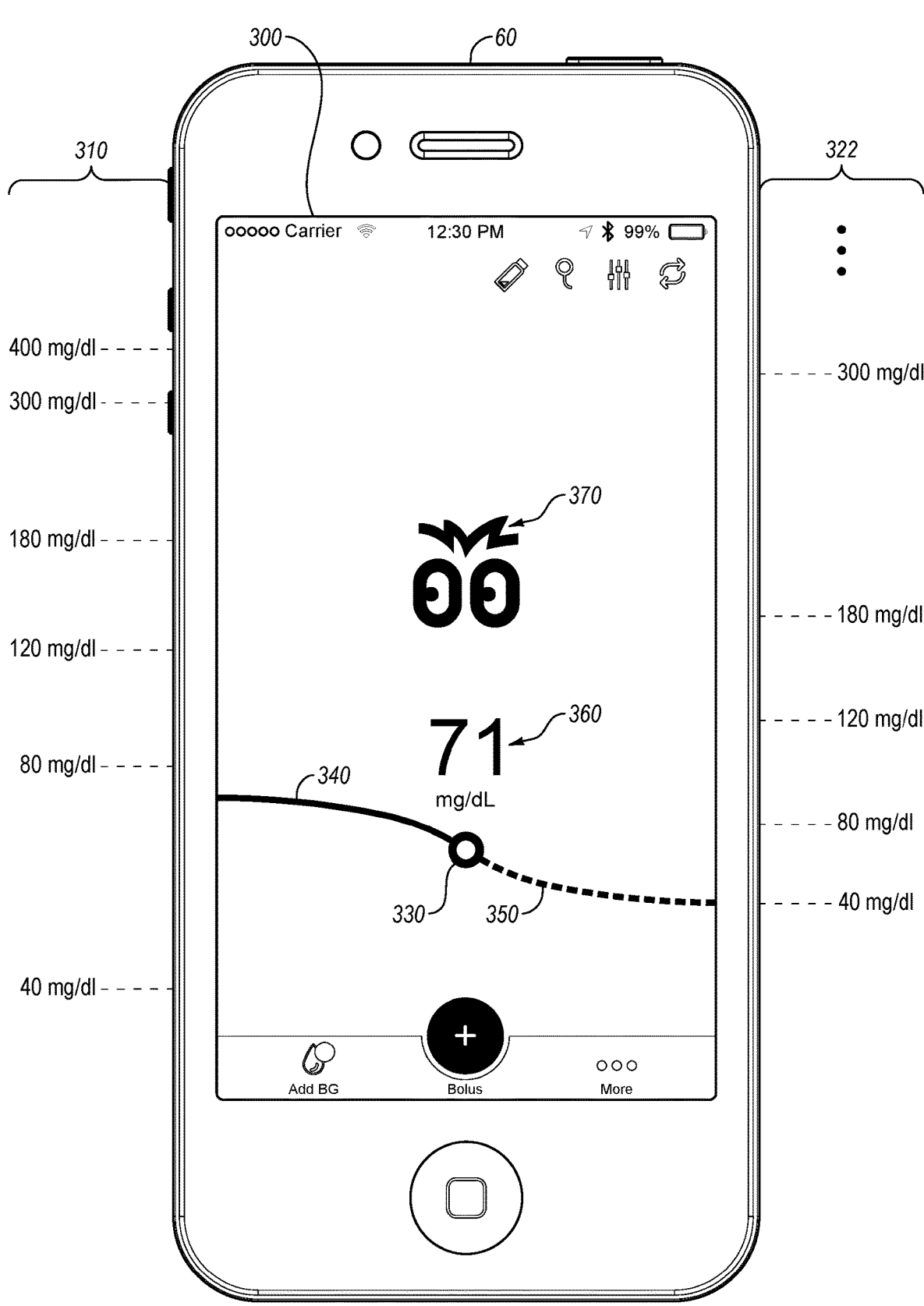
FIGS. 3A and 3B are other example displays of blood glucose information using multiple scales.
Figure 3B:
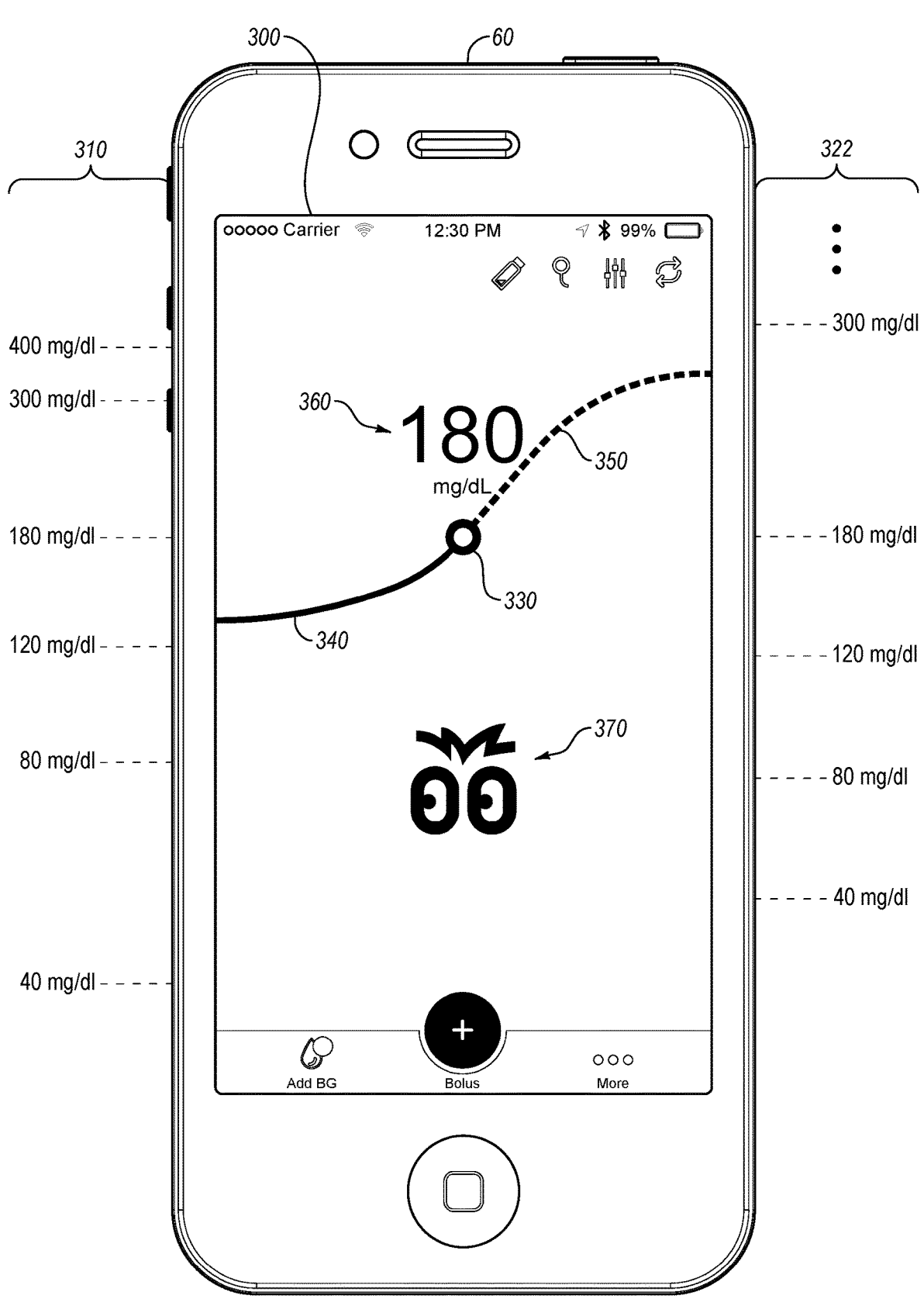

FIGS. 3A and 3B are other example displays 300 of blood glucose information using multiple scales, in accordance with one or more embodiments of the present disclosure. FIGS. 3A and 3B are similar to FIG. 2, with the variation that a second scale 322 is anchored differently than in FIG. 2.

As illustrated in FIGS. 3A and 3B, the second scale 322 may be anchored along the vertical axis of the display 300 based on the location of the current blood glucose level 330 based on the first scale 310. For example, the current blood glucose level 330 illustrated in FIG. 3A is approximately 71 mg/dL. The second scale 322 may be shifted along the vertical axis of the display 300 such that the current blood glucose level 330, located along the vertical axis in the first scale 310, is also at the same vertical position along the vertical axis of the display 300. The second scale 322 may be anchored in the vertical axis based on the current blood glucose level 330 according to the first scale 310. As another example, as illustrated in FIG. 3B, the current blood glucose level 330 is approximately 180 mg/dL, and the second scale 322 is anchored to that value according to the first scale 310.

As illustrated in FIG. 3A, the current blood glucose level 330 of 71 mg/dl may be displayed along the vertical axis of the display 300 according to the first scale 310. The historical blood glucose levels 340 may be displayed relative to the current blood glucose level 330 according to the second scale 322. For example, a continuous line from 71 mg/dL may proceed back in time up to approximately 85 mg/dL on the second scale 322 (while if the first scale 310 were used the historical blood glucose levels 340 would indicate only approximately 75 mg/dL). As another example, a continuous line from 71 mg/dL may proceed forward in time down to approximately 40 mg/dL for the projected blood glucose levels 350 according to the second scale 322 (while if the first scale 310 were used the projected blood glucose levels 350 would only be approximately 55 mg/dL). In one embodiment, the continuous line may comprise visual indicators to show that a part of the continuous line corresponds to historical, current, and projected blood glucose levels. For example, in FIG. 3A, historical blood glucose levels 340 are shown as a solid line, current blood glucose levels 330 is shown as circle that defines a white space, and projected blood glucose levels 350 are shown as a dashed line.

In some cases, the historical blood glucose levels 340 may be smoothed in the display 300. For example, the historical blood glucose levels 340 may follow a line that is smoothed to follow a curved, rather than a jagged line. Additionally or alternatively, extrapolation may be performed on blood glucose levels in between points of actual readings to facilitate smoothing of the historical blood glucose levels 340.

In some cases, the historical blood glucose levels 340 may be corrected based on an updated and/or corrected current blood glucose level 330. For example, if a newly calibrated blood glucose monitoring device provides a current blood glucose level 330 different than what is expected from the historic readings before the calibration of the device, the historical readings may be corrected based on the updated current blood glucose level 330 to smooth the historical blood glucose levels 340.

Using such an approach, the benefit of the risk-based scale may be utilized in displaying the current blood glucose level 330 along the vertical axis of the display 300. For example, hypoglycemic blood glucose levels have a larger area of the display 300 than with a linear scale such that a PWD will have a greater visual cue of how close to hypoglycemic levels they are approaching. Additionally, by using the second scale 322 for the historic blood glucose levels 340 and/or the projected blood glucose levels 350, a PWD may be able to observe trends according to a scale with which they are more familiar or comfortable and/or that may be more intuitive to the PWD.

In some cases, the future blood glucose levels 350 and/or the historic blood glucose levels 340 may be displayed as a sparkline. For example, the future blood glucose levels 350 may be displayed without a specific scale or without a specific numerical indication of the future blood glucose levels 350. Using such an embodiment, a PWD may be provided with a sense of the direction of their future blood glucose levels 350 without being overly focused on the exact levels. Additionally or alternatively, such a sparkline may be smoothed such that no clear data points are evidenced by a sudden change in direction of the line, but rather illustrate trends. Such a sparkline may provide glanceability where a PWD may glance at the display 300 and recognize generally what their historic blood glucose levels have been (e.g., low/high) and what their predicted blood glucose levels are expected to be (e.g., trending low/high) without being overloaded with data.

In some cases, an interface of the display 300 may be invoked to view a more detailed graph of the blood glucose levels conveyed by the sparkline. For example, a PWD may swipe down on the sparkline to view a more detailed graph that includes specific data points, axis labels, numerical indicators, reference lines, trend lines, and/or any other graph feature to provide a PWD a more detailed view into historic, current, and/or future blood glucose levels.

In some cases, a background color or colors may be utilized to improve glanceability. For example, a region above the line and/or a region below the line of the historic blood glucose levels 340, current blood glucose level 330, and future blood glucose levels 350 may vary based on blood glucose levels. Such an approach can give a PWD a rapid indication of blood glucose levels. For example, the color and/or color change can be based on a threshold (e.g., 180 mg/dL (or 200 or 250 or 300) for hyperglycemic blood glucose levels and 80 mg/dL (or 70 or 50 or 40) for hypoglycemic blood glucose levels). In some cases, the color may be based on the current blood glucose level 330. Additionally or alternatively, the color and/or color change may be based on future blood glucose levels 350. In some cases the region below the line may be based on the current blood glucose levels 330 and the region above the line may be based on the future blood glucose levels 350, or vice versa. In some cases, the color change can be an instant color change, or can be based on a gradient shift as the blood glucose level changes. For example, if a PWD has a current blood glucose level of 100 mg/dL the color may be gray, and as the current blood glucose level drops below 80 mg/dL, the color may change from gray to blue. As another example, if the current blood glucose level is 160 mg/dL with a projected future blood glucose level trending up to 250 mg/dL, the color may be gray and transitioning to red such that as the projected blood glucose levels cross the threshold, the color is red. In some cases, the color yellow can be used to indicate hyperglycemia, blue can be used to indicate euglycemia, and red can be used to indicate hypoglycemia. Any color scheme may be used.

Figure 4:
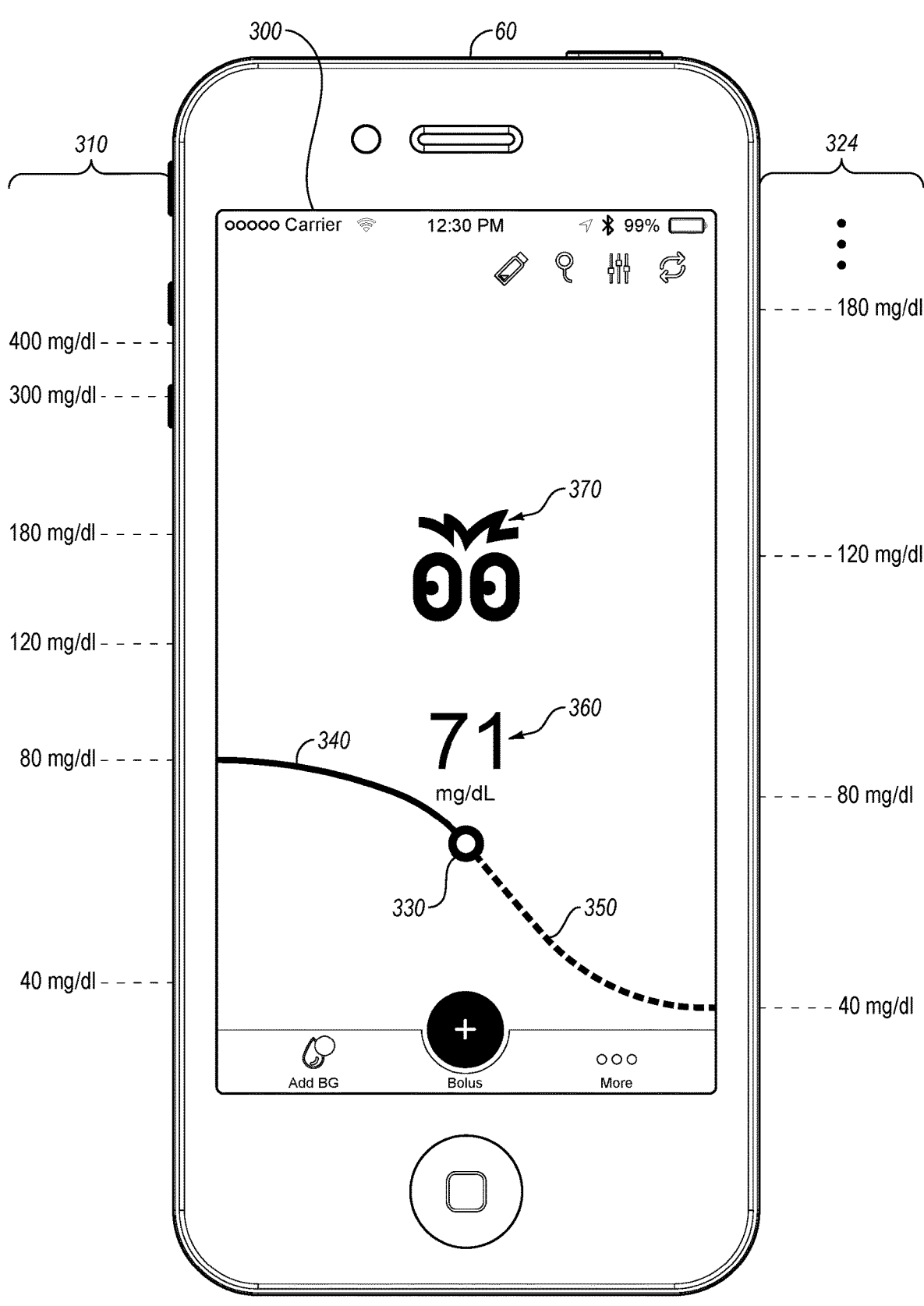
FIG. 4 is an additional example display of blood glucose information using multiple scales.

FIG. 4 is an additional example display 300 of blood glucose information using multiple scales, in accordance with one or more embodiments of the present disclosure. FIG. 4 is similar to FIGS. 3A and 3B except the second scale 324 of FIG. 4 is made larger than the second scale 322 of FIGS. 3A and 3B, while still being a linear scale and still anchored based on the first scale 310.

As illustrated in FIG. 4, the second scale 324 may be made larger such that changes in blood glucose levels and trends thereof may be more readily observed. For example, the historic blood glucose levels 340, the current blood glucose level 330, and the future blood glucose levels 350 may span from 85 mg/dL to 40 mg/dL and cover approximately 25% of the space of the display 300 based on the second scale 324. In FIGS. 3A and 3B, the same range covers approximately 12% of the display 300.

Modifications, additions, or omissions may be made to FIGS. 2-4 without departing from the scope of the present disclosure. For example, the display 300 may include numerical markings along the vertical axis of the display indicating the first scale and/or the second scale. As another example, the first scale may be any scale to emphasize certain regions of potential blood glucose levels. As an additional example, the second scale may be any magnification of the linear scale.

Figure 5:
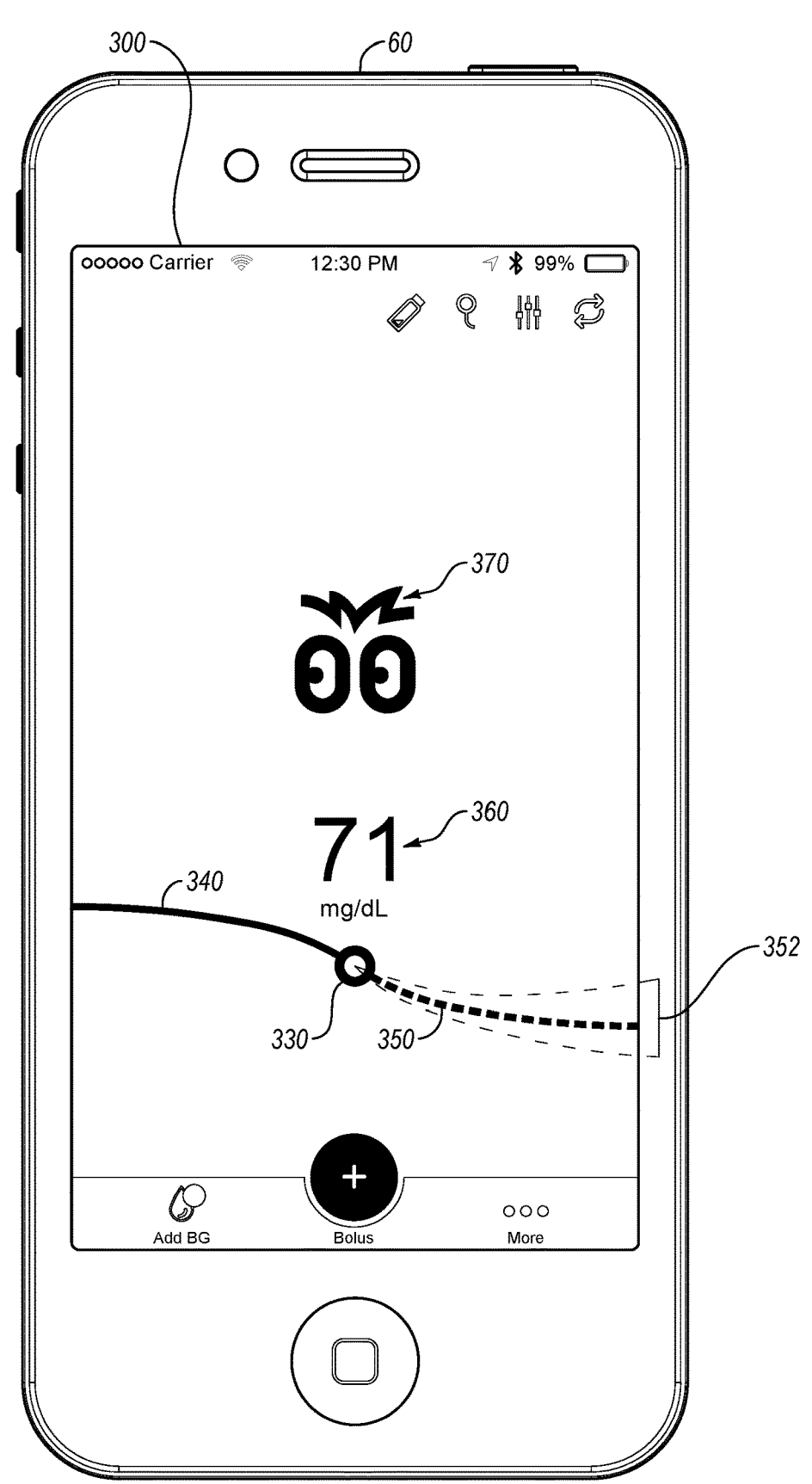
FIG. 5 is another example display of blood glucose information using multiple scales.

FIG. 5 is another example display 300 of blood glucose information using multiple scales. As illustrated in FIG. 5, in some embodiments, the projected blood glucose levels 350 may include a feature to illustrate a level of confidence in the projected blood glucose levels 350.

Depending on the approach used to project the future blood glucose levels, different future blood glucose levels may have different levels of confidence in the accuracy of the projected blood glucose levels. In some embodiments, as the projected blood glucose levels go further into the future, the confidence levels may decrease (e.g., the accuracy of the projected blood glucose level may be less and less sure).

In some embodiments, the level of confidence may be illustrated by a range 352 of potential future blood glucose levels. For example, the range 352 may illustrate that the projected future blood glucose levels close to the current blood glucose level 330 may be only a small range of values, and as the projected blood glucose levels go further into the future, the range 352 increases. The level of confidence may be illustrated in any manner, such as by error bars, maximum and/or minimum values, color changes, transparency, etc.

Modifications, additions, or omissions may be made to FIG. 5 without departing from the scope of the present disclosure. For example, the display 300 may include any approach to display confidence levels of the projected blood glucose levels.

Figure 6B:
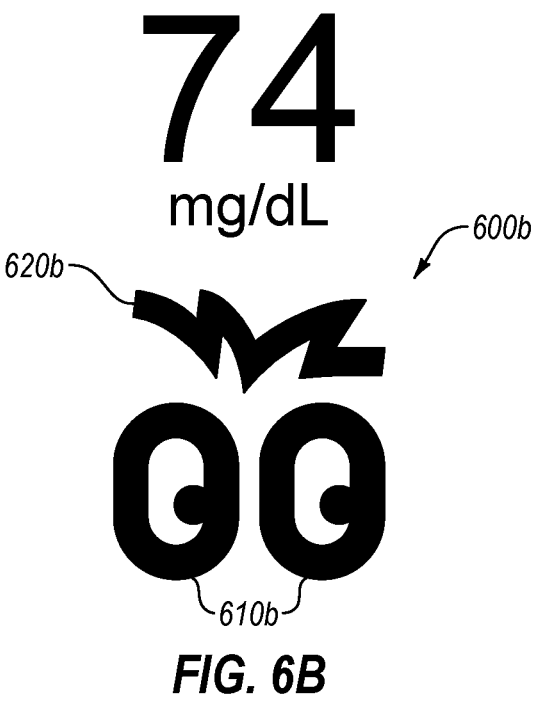

FIGS. 6A and 6B illustrate example features of a display of blood glucose information, in accordance with one or more embodiments of the present disclosure. For example, FIG. 6A illustrates a first avatar 600a and FIG. 6B illustrates a second avatar 600b. The first avatar 600a and the second avatar 600b may correspond to the same PWD but at different points in time.

The avatar 600a may include features to facilitate glanceability (which may be further characterized as glanceable, which means understandable at a glance or with occasional glances) regarding blood glucose information and/or operation of a diabetes management system (such as the system 10 of FIG. 1). In some embodiments, the avatar 600a may include a facial avatar with various features of the avatar 600a associated with various blood glucose information and/or aspects of the operation of the diabetes management system.

In some embodiments, the eyes 610a may represent the current blood glucose information. For example, whether the pupils of the eyes 610a are on the left or the right of the eyeballs may indicate whether the current blood glucose level is above or below a threshold. As another example, the pupils of the eyes 610a may be at an approximate location along the vertical length of the eyeball correlated with the vertical length of a display (such as the display 300).

In some embodiments, the eyebrows 620a may represent trends of historical and/or projected blood glucose levels. For example, if the historical blood glucose levels were higher than the current blood glucose level, the left side of the eyebrows 620a may be tilted in an upward direction and if the historical blood glucose levels were lower than the current blood glucose level, the left side of the eyebrows 620a may be tilted in a downward or lower direction. As another example, if the trend of the projected blood glucose levels are approximately the same as the current blood glucose levels, the right side of the eyebrows 620a may be relatively level. Alternatively, if the trend of the projected blood glucose levels are higher than the current blood glucose level, the right side of the eyebrows 620a may be curved upwards.

In some embodiments, a color of the avatar may shift and/or change based on blood glucose information and/or operation of the diabetes management system. For example, if the PWD is projected to have low blood sugar level below a threshold or the current blood glucose level is below a threshold, the coloration of the avatar may change to a warning color such as red. As another example, if the PWD is trending toward higher blood glucose levels, the tone of the color of the avatar 600a may get lighter and if trending toward lower blood glucose levels, the tone of the color of the avatar 600a may get darker. In some cases, the color change may be a background shading of the avatar 600a and may change in a similar manner as described for the background color. For example, the color, shade, etc., of the avatar 600a may change based on whether a blood glucose level is hyperglycemic, euglycemic, or hypoglycemic.

FIG. 6B provides an illustration of changes from the avatar 600a to avatar 600b as the blood glucose level transitions from 104 mg/dL to 74 mg/dL. For example, eyebrows 620b of the avatar 600b are raised on the left, indicating that the historical values (e.g., 104 mg/dL) are higher than the present value. As another example, the pupils of the eyes 610b may transition to the right side of the eyeball as the blood glucose level may have dropped below a threshold value.

While described in terms of blood glucose information, any aspect of blood glucose information and/or operation of the diabetes management system is contemplated. For example, a feature of the avatar 600a may correspond to whether or not the diabetes management system is providing personalized basal insulin delivery. As another example, a feature of the avatar may be related to whether or not there is an error or malfunction in the diabetes management system 10, such as an occlusion in an insulin pump.

Modifications, additions, or omissions may be made to FIGS. 6A and 6B without departing from the scope of the present disclosure. For example, the avatars 600a and/or 600b may be correlated with any aspect of blood glucose information and/or any aspect of operation of the diabetes management system. As another example, while illustrated as a facial avatar, any multi-component image or avatar may be used.

Figure 7:
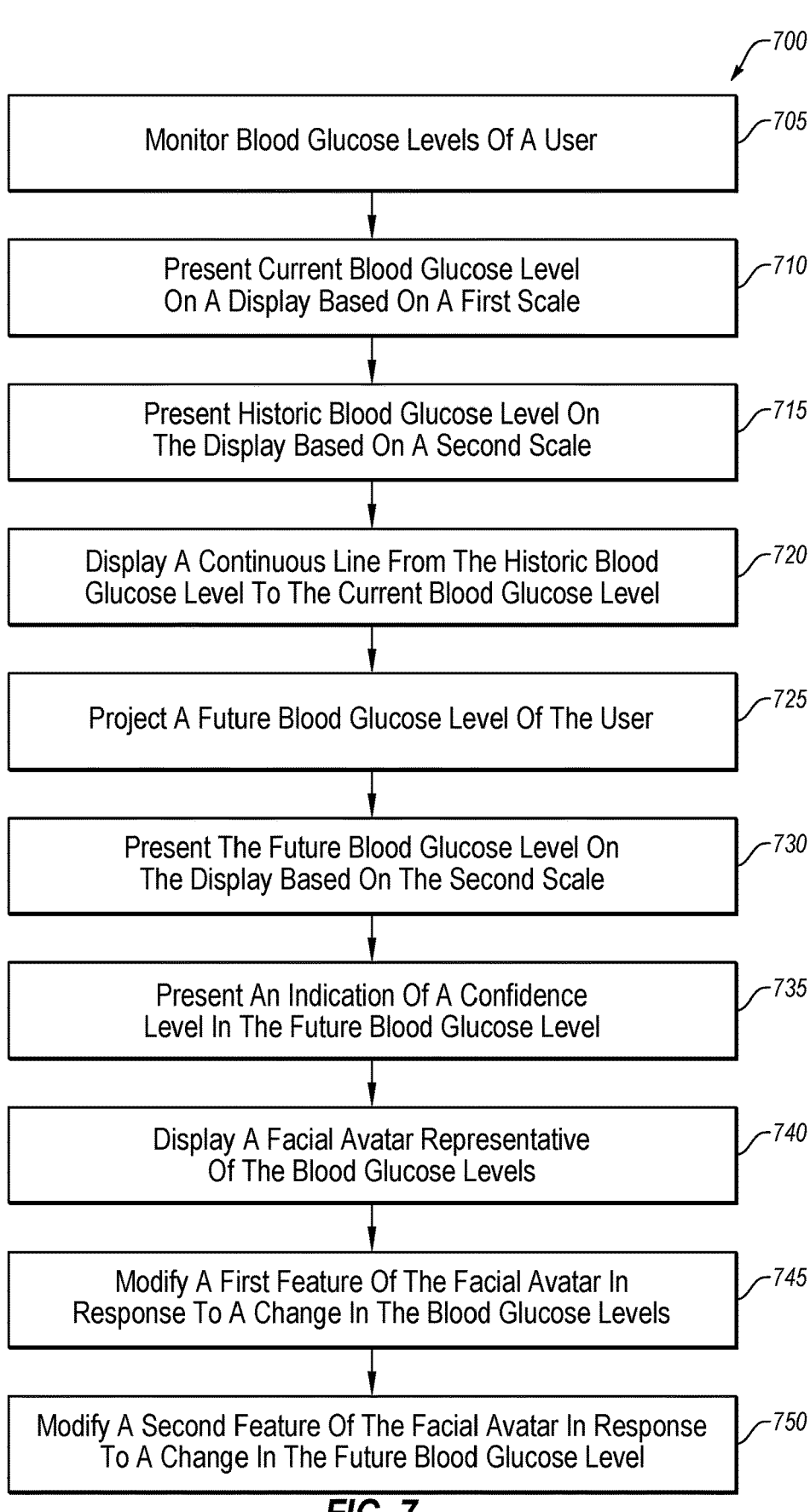
FIG. 7 illustrates a flowchart of an example method of displaying blood glucose information using multiple scales.

FIG. 7 illustrates a flow diagram of an example method 700 of presenting blood glucose information using multiple scales. The method 700 may be performed by any suitable system, apparatus, or device. For example, the system 10, the pump assembly 15, the display device 60 of FIG. 1, and/or a remote server may perform one or more of the operations associated with the method 700. Although illustrated with discrete blocks, the steps and operations associated with one or more of the blocks of the method 700 may be divided into additional blocks, combined into fewer blocks, or eliminated, depending on the desired implementation.

At block 705, blood glucose levels may be monitored for a PWD. For example, a diabetes management system (such as the system 10 of FIG. 1) may monitor the blood glucose levels using a CGM and/or a BGM. In these and other embodiments, a single device may monitor the blood glucose levels or a separate device may obtain the blood glucose levels from a monitoring device.

At block 710, a current blood glucose level may be presented on a display based on a first scale. For example, the current blood glucose level may be displayed at a first location along the vertical axis of the display based on a first scale, such as a risk-based scale. The risk-based scale may include a logarithmic scale.

At block 715, historic blood glucose levels may be presented on the display based on a second scale. For example, the historic blood glucose levels may be displayed at a second location based on the second scale and the location of the current blood glucose level. For example, the second scale may be anchored to the location of the current blood glucose level. The second scale may include a linear scale.

At block 720, a continuous line may be displayed from the current blood glucose level to one or more of the historic blood glucose levels. For example, a line may be extrapolated between the current blood glucose level and a historic level such that a continuous line may be displayed.

At block 725, a future blood glucose level of the user may be projected.

At block 730, the projected future blood glucose level of the block 725 may be presented on the display based on the second scale. For example, the future blood glucose level may be presented according to the same scale as the historic blood glucose levels. Additionally or alternatively, a continuous line may be displayed connecting the future blood glucose level and the current blood glucose level.

At block 735, an indication of a confidence level in the future blood glucose level may be presented.

At block 740, a facial avatar representative of the blood glucose levels may be displayed. Additionally or alternatively, another type of avatar or other multi-feature image may be displayed.

At block 745, a first feature of the facial avatar may be modified in response to a change in the blood glucose levels. For example, based on a newly received blood glucose level the first feature may be modified. As another example, the first feature may be modified based on changes to trends in blood glucose levels (e.g., based on historical blood glucose levels).

At block 750, a second feature of the facial avatar may be modified in response to a change in the future blood glucose level. For example, the second feature may be modified based on a trend associated with the future blood glucose level or a projected blood glucose level.

Modifications, additions, or omissions may be made to the method 700 without departing from the scope of the present disclosure. For example, the operations of the method 700 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer-readable storage media including Random-Access Memory (RAM), Read-Only Memory (ROM), Electrically Erasable Programmable Read-Only Memory (EEPROM), Compact Disc Read-Only Memory (CD-ROM) or other optical disc storage, magnetic disk storage or other magnetic storage devices, Flash memory devices (e.g., solid state memory devices), or any other storage medium that may be used to carry or store desired program code in the form of computer-executable instructions or data structures and which may be accessed by a general-purpose or special-purpose computer. Combinations of the above may also be included within the scope of computer-readable media.

Computer-executable instructions comprise, for example, instructions and data which cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general-purpose hardware (e.g., computer-readable media, processing devices, etc.) of the computing system. In some embodiments, the different components, modules, engines, and services described herein may be implemented as objects or processes that execute on the computing system (e.g., as separate threads). Routines and operations performed by a processor, machine-readable instructions that a processor executes to perform such routines and operations, and functions that such routines and operations enable, may be described herein as an "algorithm" or a number of related "algorithms." While some of the system and methods described herein are generally described as being implemented in software (stored on and/or executed by general-purpose hardware), specific hardware implementations or a combination of software and specific hardware implementations are also possible and contemplated. In the present description, a "computing entity" may be any computing system as previously defined herein, or any module or combination of modulates running on a computing system.

Any ranges expressed herein (including in the claims) are considered to be given their broadest possible interpretation. For example, unless explicitly mentioned otherwise, ranges are to include their end points (e.g., a range of "between X and Y" would include X and Y). Additionally, ranges described using the terms "approximately" or "about" are to be understood to be given their broadest meaning consistent with the understanding of those skilled in the art. Additionally, the term approximately includes anything within 10%, or 5%, or within manufacturing or typical tolerances.

All examples and conditional language recited herein are intended for pedagogical objects to aid the reader in understanding the disclosure and the concepts contributed by the inventor to furthering the art and are to be construed as being without limitation to such specifically recited examples and conditions. Although embodiments of the present disclosure have been described in detail, it should be understood that the various changes, substitutions, and alterations could be made hereto without departing from the spirit and scope of the disclosure.

One or more non-limiting embodiments of the disclosure include:

Embodiment 1. A method of displaying blood glucose information, the method comprising: monitoring blood glucose levels of a user, the blood glucose levels including at least a current blood glucose level and a historic blood glucose level; presenting the current blood glucose level at a first location on a display based on a first scale; and presenting the historic blood glucose level at a second location on the display based on a second scale different from the first scale.

Embodiment 2. The method of Embodiment 1, wherein the first scale is a logarithmic scale, such that and blood glucose values below a threshold correspond to a larger area of the display than blood glucose levels above the threshold.

Embodiment 3. The method of Embodiment 2, wherein the threshold includes approximately 200 mg/dL.

Embodiment 4. The method of one of Embodiments 1-3, further comprising: projecting a future blood glucose level of the user; and presenting the future blood glucose level of the user at a third location on the display based on the second scale.

Embodiment 5. The method of Embodiment 4, further comprising presenting an indication of a confidence level in the future blood glucose level.

Embodiment 6. The method of one of Embodiments 1-5, wherein the second scale is a linear scale.

Embodiment 7. The method of one of Embodiments 1-6, wherein the second location is based on the second scale relative to the first location.

Embodiment 8. The method of one of Embodiments 1-7, wherein the first location is based on the first scale relative to a vertical axis of the display.

Embodiment 9. The method of one of Embodiments 1-8, further comprising displaying a continuous line from the first location to the second location according to the first scale.

Embodiment 10. The method of one of Embodiments 1-9, wherein the continuous line is a dashed line.

Embodiment 11. The method of one of Embodiments 1-10, further comprising: displaying a facial avatar representative of the blood glucose levels; modifying a first feature of the facial avatar in response to a change in the blood glucose levels; and modifying a second feature of the facial avatar in response to a change in a projected future blood glucose level.

Embodiment 12. The method of Embodiment 11, wherein the first feature includes eyes of the facial avatar and wherein a location of the eyes corresponds to the current blood glucose level.

Embodiment 13. The method of one of Embodiment 11 or Embodiment 12, wherein the second feature of the facial avatar includes eyebrows of the facial avatar and wherein an orientation of the eyebrows corresponds to the projected future blood glucose level.

Embodiment 14. A device for displaying blood glucose information, the device comprising: a display; one or more processors; and a non-transitory computer-readable medium containing instructions that, when executed by the one or more processors, cause the device to perform operations, the operations comprising: obtain monitored blood glucose levels for a user, the blood glucose levels including at least a current blood glucose level and a historic blood glucose level; present the current blood glucose level at a first location on the display based on a first scale; and present the historic blood glucose level at a second location on the display based on a second scale different from the first scale.

Embodiment 15. The device of Embodiment 14, further comprising a blood glucose monitor by which the device obtains the monitored blood glucose levels.

Embodiment 16. The device of one of Embodiment 14 or Embodiment 15, further comprising a communication device configured to communicate with a blood glucose monitoring device via which the device obtains the monitored blood glucose levels.

Embodiment 17. The device of one of Embodiments 14-16, wherein the operations further comprise: project a future blood glucose level of the user; and present the future blood glucose level of the user at a third location on the display based on the second scale.

Embodiment 18. A system for displaying blood glucose information, the system comprising: a blood glucose monitoring device configured to monitor blood glucose levels of a user; a display; one or more processors; and a non-transitory computer-readable medium containing instructions that, when executed by the one or more processors, cause the system to perform operations, the operations comprising: obtain the blood glucose levels from the blood glucose monitoring device, the blood glucose levels including at least a current blood glucose level and a historic blood glucose level; present the current blood glucose level at a first location on the display based on a first scale; and present the historic blood glucose level at a second location on the display based on a second scale different from the first scale.

Embodiment 19. The system of Embodiment 18, further comprising a communication device configured to communicate with the blood glucose monitoring device to obtain the monitored blood glucose levels.

Embodiment 20. The system of one of Embodiment 18 or Embodiment 19, wherein the operations further comprise: project a future blood glucose level of the user; and present the future blood glucose level of the user at a third location on the display based on the second scale.

20

What is claimed is:

1. A method of displaying glucose information, the method comprising:
monitoring glucose levels of a user, the glucose levels including at least a current glucose level and a historic glucose level;
presenting a value representative of blood glucose as a plot point at a first location along a center vertical axis of a display based on a logarithmic scale, the value representative of blood glucose comprising the current glucose level;
presenting a further value representative of blood glucose as a further plot point at a second location on the display based on a linear scale, the further value representative of blood glucose at least partially based on the historic glucose level,
wherein the value presented at the first location and the further value presented at the second location are presented on the display simultaneously;
shifting the plot point to a third location along the center vertical axis of the display responsive to a change of the current glucose level;
responsive to the plot point shifting to the third location along the center vertical axis of the display, adjusting the linear scale upon which the second location of the further value is based by adjusting an anchor of the linear scale along the center vertical axis in a same direction in which the plot point was shifted to the third location along the center vertical axis; and
shifting the further plot point to a fourth location on the display based on the adjusted linear scale.

2. The method of claim 1, wherein values presented on the logarithmic scale below a threshold correspond to a larger area of the display than glucose levels presented on logarithmic scale above the threshold.

3. The method of claim 2, wherein the threshold includes approximately 200 mg/dL.

4. The method of claim 1, further comprising:
calculating a future glucose level of the user; and
presenting a yet further value representative of blood glucose at a fifth location on the display based on the linear scale, the yet further value representative of blood glucose at least partially based on the future glucose level of the user.

5. The method of claim 4, further comprising presenting an indication of a confidence level in the future glucose level.

6. The method of claim 1, wherein the further plot point is displayed according to the linear scale and relative to the plot point.

7. The method of claim 1, further comprising displaying a continuous line according to the linear scale and extending from the further value to the value.

8. The method of claim 7, wherein the continuous line is a solid line.

9. The method of claim 1, further comprising:
displaying a facial avatar representative of the value;
modifying a first feature of the facial avatar in response to a change in glucose level; and
modifying a second feature of the facial avatar in response to a change in future glucose level.

10. The method of claim 9, wherein the first feature includes eyes of the facial avatar and wherein a location of the eyes corresponds to the value.

11. The method of claim 10, wherein the second feature of the facial avatar includes eyebrows of the facial avatar and wherein an orientation of the eyebrows corresponds to a future glucose level.

12. A device for displaying glucose information, the device comprising:

a display;

one or more processors; and a non-transitory computer-readable medium containing instructions that, when executed by the one or more processors, cause the device to perform operations, the operations comprising:

obtain monitored glucose levels for a user, the glucose levels including at least a current glucose level and a historic glucose level;

present a value representative of blood glucose as a plot point at a first location along a center vertical axis of the display based on a logarithmic scale, the value representative of blood glucose comprising the current glucose level;

present a further value representative of blood glucose as a further plot point at a second location on the display based on a linear scale, the further value representative of blood glucose at least partially based on the historic glucose level, wherein the value presented at the first location and the further value presented at the second location are presented on the display simultaneously;

shift the plot point to a third location along the center vertical axis of the display responsive to a change of the current glucose level;

responsive to the plot point shifting to a third location along the center vertical axis of the display, adjust the linear scale upon which the second location of the further value is based by adjusting an anchor of the linear scale along the center vertical axis in a same direction in which the plot point was shifted to the third location along the center vertical axis; and shift the further plot point to a fourth location on the display based on the adjusted linear scale.

13. The device of claim 12, further comprising a communication device configured to communicate with a glucose monitoring device via which the device obtains the monitored glucose levels.

14. The device of claim 12, wherein the operations further comprise:

calculate a future glucose level of the user; and present a yet further value representative of blood glucose at a fifth location on the display based on the linear scale, the yet further value representative of blood glucose at least partially based on the future glucose level of the user.

15. A system for displaying glucose information, the system comprising:

a glucose monitoring device configured to monitor glucose levels of a user;

a display;

one or more processors; and a non-transitory computer-readable medium containing instructions that, when executed by the one or more processors, cause the system to perform operations, the operations comprising:

obtain the glucose levels from the glucose monitoring device, the glucose levels including at least a current glucose level and a historic glucose level;

present a value representative of blood glucose as a plot point at a first location along a center vertical axis of the display based on a logarithmic scale, the value representative of blood glucose comprising the current glucose level; and present a further value representative of blood glucose as a further plot point at a second location on the display based on a linear scale, the further value representative of blood glucose at least partially based on the historic glucose level, wherein the value presented at the first location and the further value presented at the second location are presented on the display simultaneously;

shift the plot point to a third location along the center vertical axis of the display responsive to a change of the current glucose level;

responsive to the plot point shifting to a third location along the center vertical axis of the display, adjust the linear scale upon which the second location of the further value is based by adjusting an anchor of the linear scale along the center vertical axis in a same direction in which the plot point was shifted to the third location along the center vertical axis; and shift the further plot point to a fourth location on the display based on the adjusted linear scale.

16. The system of claim 15, further comprising a communication device configured to communicate with the glucose monitoring device to obtain the monitored glucose levels.

17. The system of claim 15, wherein the operations further comprise:

calculate a future glucose level of the user; and present a yet further value representative of blood glucose at a fifth location on the display based on the linear scale, the yet further value representative of blood glucose at least partially based on the future glucose level of the user.

* * * * *